(12) United States Patent
Wang et al.

(10) Patent No.: US 11,446,390 B2
(45) Date of Patent: Sep. 20, 2022

(54) ANTIGEN CAPTURING NANOPARTICLES FOR USE IN CANCER IMMUNOTHERAPY

(71) Applicant: The University of North Carolina at Chapel Hill, Chapel Hill, NC (US)

(72) Inventors: Andrew Wang, Durham, NC (US); Yuanzeng Min, Nanjing (CN); Zach Rodgers, Kent, OH (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 350 days.

(21) Appl. No.: 15/777,075

(22) PCT Filed: Nov. 17, 2016

(86) PCT No.: PCT/US2016/062563
§ 371 (c)(1),
(2) Date: May 17, 2018

(87) PCT Pub. No.: WO2017/087692
PCT Pub. Date: May 26, 2017

(65) Prior Publication Data
US 2019/0262471 A1 Aug. 29, 2019

Related U.S. Application Data

(60) Provisional application No. 62/256,944, filed on Nov. 18, 2015.

(51) Int. Cl.
| | |
|---|---|
| A61K 47/69 | (2017.01) |
| A61P 35/00 | (2006.01) |
| A61K 39/39 | (2006.01) |
| A61K 47/34 | (2017.01) |
| A61K 47/42 | (2017.01) |
| A61K 9/19 | (2006.01) |
| A61K 9/51 | (2006.01) |
| A61K 9/00 | (2006.01) |

(52) U.S. Cl.
CPC ........ *A61K 47/6937* (2017.08); *A61K 9/0019* (2013.01); *A61K 9/19* (2013.01); *A61K 9/5123* (2013.01); *A61K 9/5146* (2013.01); *A61K 9/5153* (2013.01); *A61K 9/5169* (2013.01); *A61K 39/39* (2013.01); *A61K 47/34* (2013.01); *A61K 47/42* (2013.01); *A61P 35/00* (2018.01)

(58) Field of Classification Search
None
See application file for complete search history.

(56) References Cited

PUBLICATIONS

Hanson et al. (Biomacromolecules 2014, 15, 2475-2481) (Year: 2014).*
Sahdev et al. (Biomacromolecules 2014, 15, 2475-2481) (Year: 2014).*
Allahyari et al. (Human vaccines & immunotherapeutics, 2016, vol. 12, No. 3, 806-828) (Year: 2016).*
Jeanbart et al. (Cancer Immunol Res; 2(5) May 2014) (Year: 2014).*
Ranjan et al. (Biomed Res Int. 2014; 2014: 804680) (Year: 2014).*
Saha et al. (Anal. Chem. 2014, 86, 8158-8166) (Year: 2014).*
Arruebo et al. (Journal of Nanomaterials, vol. 2009, Article ID 439389, 24 pages) (Year: 2009).*
Choi et al. (Theranostics. 2012; 2(2): 156-178) (Year: 2012).*
Bharali, D.J., et al., "Tetraiodothyroacetic Acid-Conjugated PLGA Nanoparticles: A Nanomedicine Approach to Treat Drug-Resistant Breast Cancer," Nanomedicine, 8(12): 1943-1954 (2013).
Blencowe, C.A., et al., "Self-Immolative Linkers in Polymeric Delivery Systems," Polymer Chemistry, 2011(2): 773-790 (2011).
Hanson, M.C., et al., "Antigen Delivery By Lipid-Enveloped PLGA Microparticle Vaccines Mediated By In Situ Vesicle Shedding," Biomacromolecules, 15: 2475-2481 (2014).
Khdary, N.H., et al., "Metal-Organic-Silica Nanocomposites: Copper, Silver Nanoparticles-Ethylenediamine-Silica Gel and Their $CO_2$ Adsorption Behaviour," Journal of Materials Chemistry, 22(24): 12032-12038 (2012).
Sahdev, P., et al., "Biomaterials for Nanoparticle Vaccine Delivery Systems," Pharmaceutical Research, 31(10): 2563-2582 (2014).
PCT International Search Report and Written Opinion of the International Searching Authority for application PCT/US2016/062563 dated Feb. 16, 2017.

* cited by examiner

*Primary Examiner* — Sergio Coffa
(74) *Attorney, Agent, or Firm* — Alston & Bird LLP

(57) ABSTRACT

Disclosed herein are antigen-capturing nanoparticles. Specifically, the subject matter contained herein pertains to novel nanoparticles that can capture a multitude of tumor antigens that are released from tumor cells. Also, provided herein are methods for preparing the antigen-capturing nanoparticles and methods for the treatment of disease in a subject comprising administering the antigen-capturing nanoparticles.

19 Claims, 25 Drawing Sheets
Specification includes a Sequence Listing.

Caspase 3 Sensitive Polymer

Cathepsin B Sensitive Polymer

Matrix Metalloproteinase 2 Sensitive Polymer

```
                        SEQUENCE LISTING

<160> NUMBER OF SEQ ID NOS: 5

<210> SEQ ID NO 1
<211> LENGTH: 4
<212> TYPE: PRT
<213> ORGANISM: Artificial
<220> FEATURE:
<223> OTHER INFORMATION: Synthesized

<400> SEQUENCE: 1

Gly Phe Leu Gly
1

<210> SEQ ID NO 2
<211> LENGTH: 8
<212> TYPE: PRT
<213> ORGANISM: Artificial
<220> FEATURE:
<223> OTHER INFORMATION: Synthesized

<400> SEQUENCE: 2

Gly Pro Leu Gly Ile Ala Gly Gln
1               5

<210> SEQ ID NO 3
<211> LENGTH: 4
<212> TYPE: PRT
<213> ORGANISM: Artificial
<220> FEATURE:
<223> OTHER INFORMATION: Synthesized

<400> SEQUENCE: 3

Glu Val Asp Gly
1

<210> SEQ ID NO 4
<211> LENGTH: 6
<212> TYPE: PRT
<213> ORGANISM: Artificial
<220> FEATURE:
<223> OTHER INFORMATION: Synthesized
<220> FEATURE:
<221> NAME/KEY: MISC_FEATURE
<222> LOCATION: (1)..(1)
<223> OTHER INFORMATION: N-PEG2000

<400> SEQUENCE: 4

Asp Glu Val Asp Gly Cys
1               5

<210> SEQ ID NO 5
<211> LENGTH: 5
<212> TYPE: PRT
<213> ORGANISM: Artificial
<220> FEATURE:
<223> OTHER INFORMATION: Synthesized
<220> FEATURE:
```

```
<221> NAME/KEY: MISC_FEATURE
<222> LOCATION: (1)..(1)
<223> OTHER INFORMATION: N-PEG2000

<400> SEQUENCE: 5

Gly Phe Leu Gly Cys
1               5
```

ANTIGEN CAPTURING NANOPARTICLES FOR USE IN CANCER IMMUNOTHERAPY

CROSS-REFERENCE TO RELATED APPLICATION(S)

This application is a US national stage of PCT/US2016/062563, filed Nov. 17, 2016, which claims priority from and the benefit of U.S. Provisional Application No. 62/256,944 filed Nov. 18, 2015, the entire contents of each of which are incorporated by reference in their entirety for all purposes.

GOVERNMENT INTEREST

This invention was made with government support under Grant Number CA178748 awarded by the National Institutes of Health. The government has certain rights in the invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 513988SEQLIST_ST25.TXT, created on May 17, 2018, and having a size of 1,254 bytes and is filed concurrently with the specification. The sequence listing contained in this ASCII formatted document is part of the specification and is herein incorporated by reference in its entirety.

FIELD OF THE INVENTION

The subject matter contained herein relates generally to antigen-capturing nanoparticles (AC-NP), their formation and use in the treatment of cancer.

BACKGROUND

Cancer immunotherapy, the utilization of the patient's own immune system to treat cancer, has emerged as a powerful new strategy in cancer treatment. Recent development of antibodies that can block negative immune regulatory pathways, such as the cytotoxic T-lymphocyte-associated antigen 4 (CTLA-4) and the programmed cell death 1 (PD-1), have resulted in clinical improvements in patients with melanoma that was not seen previously. Although much of the initial focus of immunotherapy has been in patients with melanoma, growing evidence suggests that these therapeutics are effective in many other malignancies. Anti-CTLA-4 (αCTLA-4) and anti-PD-1 (αPD-1) treatments are being investigated in prostate, lung, pancreatic, bladder, renal cell, and head and neck cancers. Early clinical data suggest immunotherapy will make major impacts on these diseases as well. A major limitation of cancer immunotherapy is the low response rate. Treatment with either single agent (αCTLA-4 or αPD-1) or combination treatment results in response rates of 10-40%. Patients who do respond to these treatments have prolonged survival. Such findings have led to high interest in developing strategies to further improve cancer immunotherapy. The current cancer immunotherapy utilizing patient's tumor cells generally utilize tumor cell lysates and/or the patient's dendritic cells. But the response rates as well as the effects are low.

A different clinical approach of substantial interest to improving immunotherapy has been to combine radiotherapy with the use of immunotherapy agents. Radiotherapy has been shown to enhance immunotherapy, especially in generating the abscopal effect, a phenomenon in which local radiotherapy leads to systemic regression of metastatic cancer. First reported in the 1950's, the abscopal effect is a rare event that has been reported in patients with melanoma, renal cell carcinoma, and lymphoma. Preclinical data suggest that the abscopal effect can be enhanced by combining radiotherapy and other immunotherapy modulations. Postow et al. validated such preclinical data recently in the New England Journal of Medicine by demonstrating an abscopal effect in a patient with metastatic melanoma. Treatment regimens that can lead to the abscopal effect have the potential to turn the primary or metastatic tumors into tumor vaccines.

The mechanism of synergy between immunotherapy and radiotherapy is thought to be due to radiotherapy increasing the antigen exposure to the myeloid cells. Radiotherapy-induced cell death induces the release of many tumor antigens and enables the development of an antigenic "cascade" (expansion of T cell clones that are reactive against a variety of tumor antigens) rather than an immune response against a few antigens. This is critical to the success of immunotherapy in several ways. First, strongly immunogenic antigens are usually lost during tumor progression as tumors evade the immune system, making it difficult to select specific antigen targets. Second, past experience with cancer vaccines has demonstrated that eliciting an immune response against one or several "chosen" tumor antigens does not result in improved cancer survival. Furthermore, activation and expansion of T cells specific for the tumor antigen present in a cancer vaccine failed to correlate with tumor response in clinical trials. Such results suggest that T cells recognizing one or a few antigenic targets will have difficulty in achieving major therapeutic effects. Effective immunotherapy may rely on the immune system to recognize a multitude of antigens or antigenic cascades. Radiotherapy is known to promote this antigenic cascade. Radiotherapy can also induce the release of immune modulating molecules that can further enhance immunotherapy. For example, radiotherapy can cause the release of alarmins, endogenous molecules that can activate the immune system from dying tumor cells. One particular alarmin released by radiotherapy, HMGB1, is known to induce maturation of dendritic cells (DCs) to promote a cytotoxic T-lymphocyte response through cross presentation of tumor antigens.

Separately, a key preclinical strategy to improve antigenic response is to utilize nanoparticles to improve antigen presentation and immune response. Nanoparticle bound antigens have been shown to elicit greater immune response than free antigens. Recently, Fadel et al. demonstrated that a carbon nanotube-polymer composite could activate T-cells in immunotherapy. Moreover, data suggest that immune responses to nanoparticles can be modulated by adjusting nanoparticle size and shape. Thus far, nanoparticle based immunotherapy strategies have involved selecting and combining several known antigens with nanoparticles. As mentioned above, such strategies may not generate a therapeutic response for the same reasons that cancer vaccines have failed. The nanoparticles disclosed herein are efficient at presenting tumor generated antigens to immune cells. The data described herein show an enhanced immune therapy in tumors.

BRIEF SUMMARY

One aspect of the subject matter described herein is directed to antigen-capturing nanoparticles and to methods for preparing the antigen-capturing nanoparticles.

Another aspect of the subject matter described herein relates to methods of treating cancer comprising administering the antigen-capturing nanoparticles to a subject in cancer immunotherapy. The method involves administering the antigen-capturing nanoparticles to a subject. The method further involves treating the subject with a cancer therapy, thus providing an enhanced cancer immunotherapy.

In an embodiment, the subject matter described herein is directed to antigen-capturing nanoparticles comprising a core covalently bound to a peptide which is covalently bound to PEG.

In another embodiment, the antigen-capturing nanoparticles contain an adjuvant.

Another embodiment involves a method for making the antigen-capturing nanoparticles.

Still another embodiment involves methods of using the antigen-capturing nanoparticles.

Still further embodiments are described as herein.

BRIEF DESCRIPTION OF THE DRAWINGS

FIG. 10(a) shows the number of unique proteins bound to AC-NPs. FIG. 10(b) shows a comparison of proteins bound to AC-NPs with different surface chemistries. The composition and abundance of proteins captured by AC-NPs were compared by one-way analysis of variance (ANOVA) with Tukey's post-test. Data represent mean±standard error of the mean (SEM). P value (*, P<0.05; , P<0.01; *, P<0.005).

FIG. 11(a) shows growth curves of irradiated (primary) and unirradiated (secondary) tumors in individual mice treated with immunotherapy and AC-NP formulations. FIG. 11(b) shows average tumor growth curves of unirradiated (secondary) tumors in mice treated in FIG. 11(a). FIG. 11(c) shows survival curves of the mice in (a). (Control, n=10; RT, n=10; RT+αPD-1, n=9; mPEG AC-NPs+RT+αPD-1, n=10; NH2 AC-NPs+RT+αPD-1, n=9; PLGA AC-NPs+RT+αPD-1, n=10; Mal AC-NPs+RT+αPD-1, n=8; PLGA AC-NPs (in unirradiated tumor)+RT+αPD-1, n=10). Tumor growth over time was compared by two-way analysis of variance (ANOVA) with Bonferroni correction. Data represent mean±standard error of the mean (SEM). Differences in survival were determined for each group by the Kaplan-Meier method and the overall P value was calculated by the log-rank test. P value (*, P<0.05; , P<0.01; *, P<0.005).

FIG. 12(a) shows an image of sentinel lymph nodes after intratumoral injection of fluorescently-labeled AC-NPs and quantification of fluorescence intensity in these lymph nodes (n=5). FIG. 12(b) shows flow cytometric analysis quantifying the percent of antigen presenting dendritic cells (CD11c$^+$), macrophages (F4/80$^+$), and B cells (B220$^+$) with fluorescently-labeled AC-NPs (Mal AC-NPs, n=4; mPEG AC-NPs+RT, n=3; PLGA AC-NPs+RT, n=4; Mal AC-NPs+RT, n=4). FIG. 12(c) shows flow cytometric analysis assessing the relative abundance of CD8$^+$, CD4$^+$, and CD4$^+$FOXP3$^+$ T cell subpopulations (RT, n=10; αPD-1, n=9; RT+αPD-1, n=10; Mal AC-NPs+RT+αPD-1, n=10). T cells were defined as being CD45+CD3$^+$. FIG. 12(d) shows flow cytometric analysis evaluating IFN-γ secreting T cells in spleens of animals treated with AC-NPs and subsequently stimulated ex vivo with cancer derived antigens (RT, n=10; αPD-1, n=9; RT+αPD-1, n=10; Mal AC-NPs+RT+αPD-1, n=10). T cells in this assay were defined as CD3$^+$. Statistical significance was assessed using analysis of unpaired t test. Data represent mean±standard error of the mean (SEM). P value (*, P<0.05; , P<0.01; *, P<0.005).

FIG. 13(a) shows tumor growth curves of individual animals treated with immunotherapy and AC-NPs. FIG. 13(b) shows average tumor growth curves shown in FIG. 13(a). FIG. 13(c) shows survival curves of mice in (a) (n=8). Tumor growth over time was compared by two-way analysis of variance (ANOVA) with Bonferroni correction. Data represent mean±standard error of the mean (SEM). Differences in survival were determined for each group by the Kaplan-Meier method and the overall P value was calculated by the log-rank test. P value (*, P<0.05; , P<0.01; *, P<0.005).

FIG. 24(a) shows growth curves of irradiated (primary) and unirradiated (secondary) tumors in individual mice treated with immunotherapy and AC-NP formulations. FIG. 24(b) shows average tumor growth curves of unirradiated (secondary) tumors in mice treated in FIG. 24(a). FIG. 24(c) shows survival curves of the mice in FIG. 24(a). (n=6). Tumor growth over time was compared by Dunnett's Multiple Comparison Test. Data represent mean±standard error of the mean (SEM). Differences in survival were determined for each group by the Kaplan-Meier method and the overall P value was calculated by the log-rank test. P value (*, $P<0.05$; , $P<0.01$; *, $P<0.005$).

DETAILED DESCRIPTION

Figure 1:
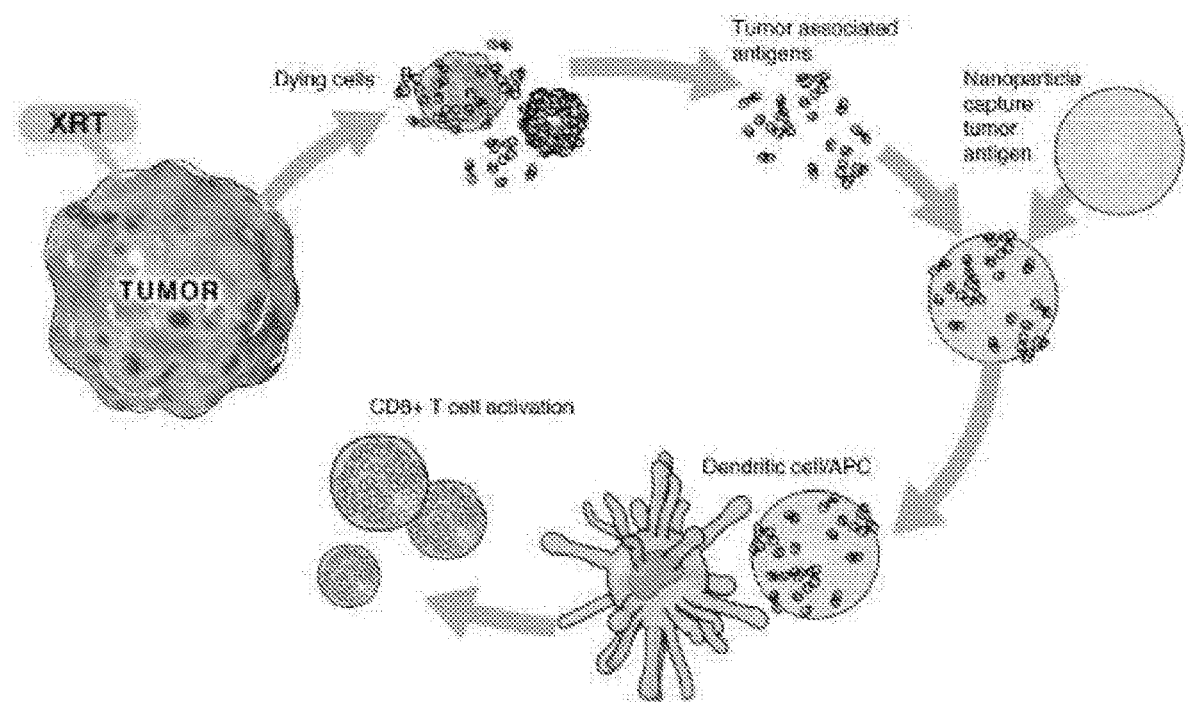
FIG. 1 depicts an example of antigen capturing nanoparticles for use in cancer immunotherapy.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

Described herein are biodegradable and biocompatible AC-NPs that can enhance cancer immunotherapy and induce the abscopal effect. AC-NPs enhance the presentation of cancer-derived proteins by APCs, resulting in a more robust activation of cytotoxic and helper T cells. A continuing challenge that limits the effectiveness of cancer therapy is tumor heterogeneity within individual patients and among patient populations. Traditional strategies of enhancing the immunotherapeutic response by administering one or several "chosen" antigens remain unsuccessful (Melief, C. J., van Hall, T., Arens, R., Ossendorp, F. & van der Burg, S. H., *J. Clin. Invest.* 125:3401-3412(2015)), perhaps because this approach fails to account for tumor cell diversity. In contrast to traditional methods, the methods disclosed herein exposes the immune system to a wide variety of tumor derived protein antigens (TDPAs) in a patient specific manner. This treatment approach carries important implications for the advancement of personalized medicine. Importantly, the AC-NP based approach described herein can be synergistic with the existing clinical immunotherapy treatment regimen, and the AC-NPs formulations described herein contain FDA generally regarded as safe (GRAS) materials, allowing for rapid clinical translation. Thus, the subject matter described herein can potentially facilitate precision medicine with personalized immunotherapy and improve the outcome of patients suffering from cancer including extensive metastatic disease.

Herein is described antigen-capturing nanoparticle (AC-NP) formulations for use in cancer immunotherapy. The AC-NP are comprised of polymer cores that in embodiments have surface modifications that allow for binding of antigens. In an embodiment, the nanoparticles are formulated using poly (lactic-co-glycolic acid) (PLGA), a biocompatible and biodegradable polymer. In another embodiment, the nanoparticles' surfaces were modified to enable binding of TDPAs by a variety of mechanisms. Without being bound by theory, it is believed that unmodified PLGA nanoparticles bind to proteins through non-covalent hydrophobic-hydrophobic interactions, AC-NPs coated with amine-polyethylene glycol ($NH_2$-PEG) ($NH_2$ AC-NP) bind to proteins via ionic interactions, and AC-NPs coated with maleimide-PEG (Mal AC-NP) bind to proteins by reaction with thiol groups through formation of a thioether bond. In an embodiment, AC-NPs with methoxy-PEG (mPEG) were formulated, which should have minimal interactions with proteins (Jokerst, J. V., Lobovkina, T., Zare, R. N. & Gambhir, S. S., *Nanomedicine (Lond)* 6:715-728(2011)).

Figures 10A, 10B:
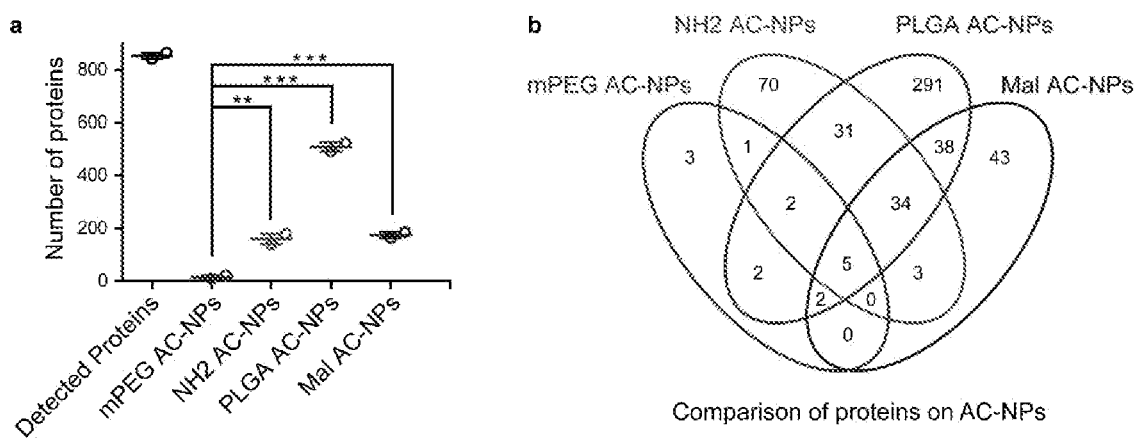
FIG. 10(a)-10(b) shows the capture of cancer derived proteins by AC-NPs is dependent upon their surface chemistry.

Studies were performed to assess the impact of the surface chemistry of nanoparticles on TDPA capture. AC-NPs were incubated with lethally irradiated B16F10 melanoma cell lysates ex vivo. Both size and zeta potential of AC-NPs changed following protein capture (FIG. 14), indicating protein capture by the nanoparticles. AC-NPs and bound proteins were then isolated by centrifugation and filtration. Mass spectrometry was used to identify the nanoparticle-associated proteins. Without being bound by theory, it is believed the diversity and composition of proteins captured by AC-NPs are dependent upon their surface chemistries. Of the nanoparticle formulations tested, the PLGA AC-NP formulation captured the most comprehensive TDPAs, while mPEG AC-NP captured very few proteins, consistent with its anti-biofouling surface (FIG. 10(a)). Some proteins were captured by multiple AC-NP formulations and some were captured by only one AC-NP formulation (FIG. 10(b)). Notably, AC-NPs were able to bind a number of alarmins (including HMGB1) and histone proteins, both of which have been shown to elicit anti-tumoral immune responses. The positive charge of amine terminated AC-NPs was believed to provide more immunogenicity; however, the data provided herein do not support this theory. Without being bound by theory, it is believed that this effectiveness goes to the mechanism by which the current nanoparticles function such that the amine terminated AC-NPs did not have a specific immune response. As such, AC-NPs capture a myriad of TDPAs that are released from radiotherapy.

Figures 11A, 11B, 11C:
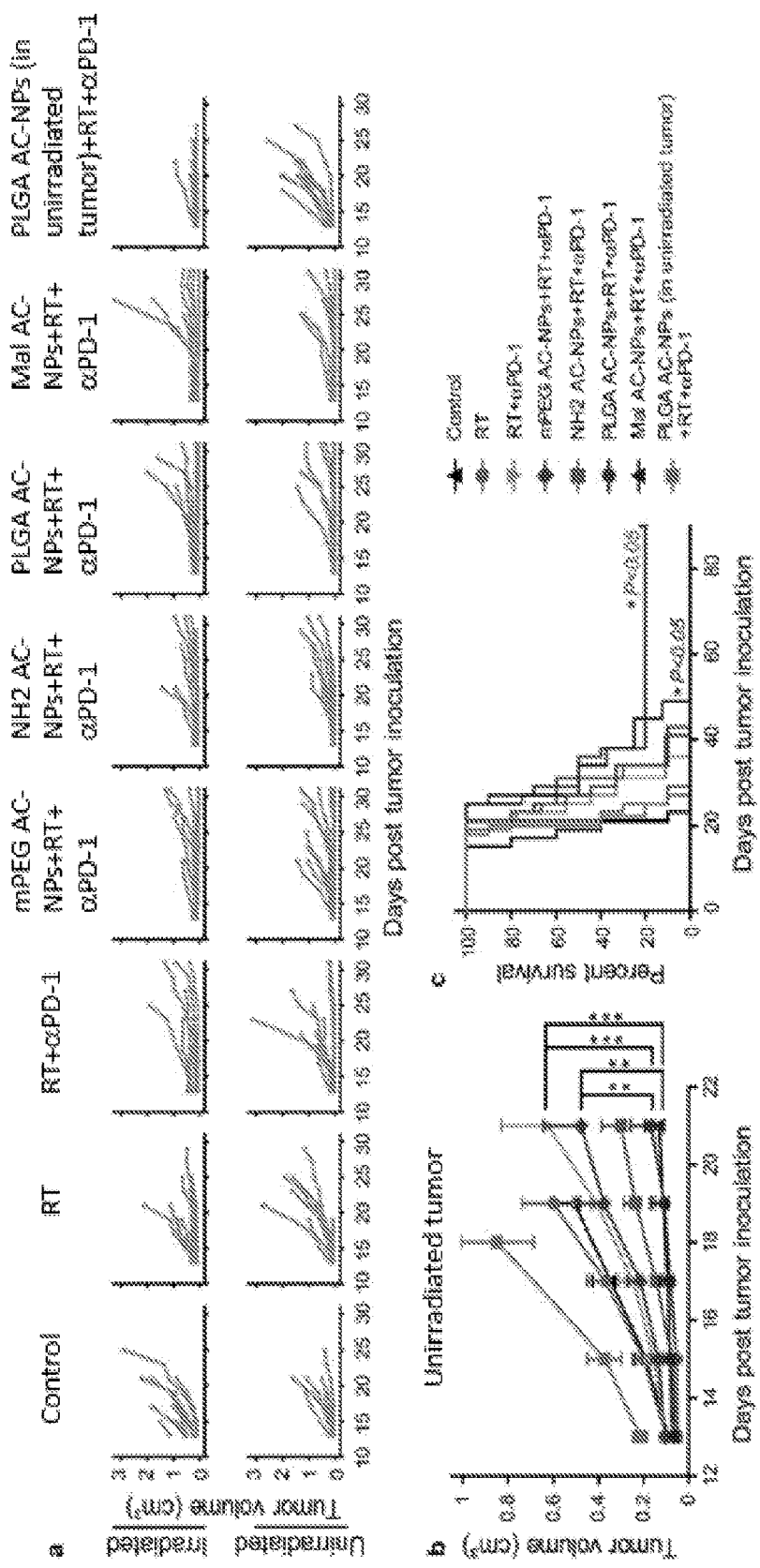
FIGS. 11(a)-11(c) show the AC-NPs can enhance immunotherapy and the abscopal effect.
Figures 15A, 15B:
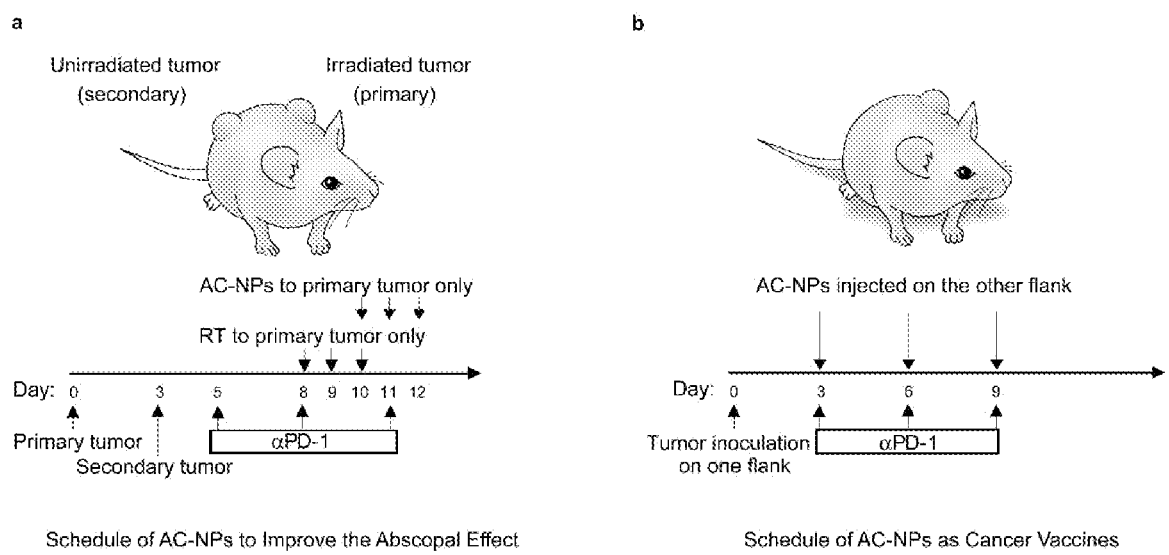
FIGS. 15(a)-15(b) depict treatment timelines of in vivo cancer immunotherapy experiments.
Figures 24A, 24B, 24C:
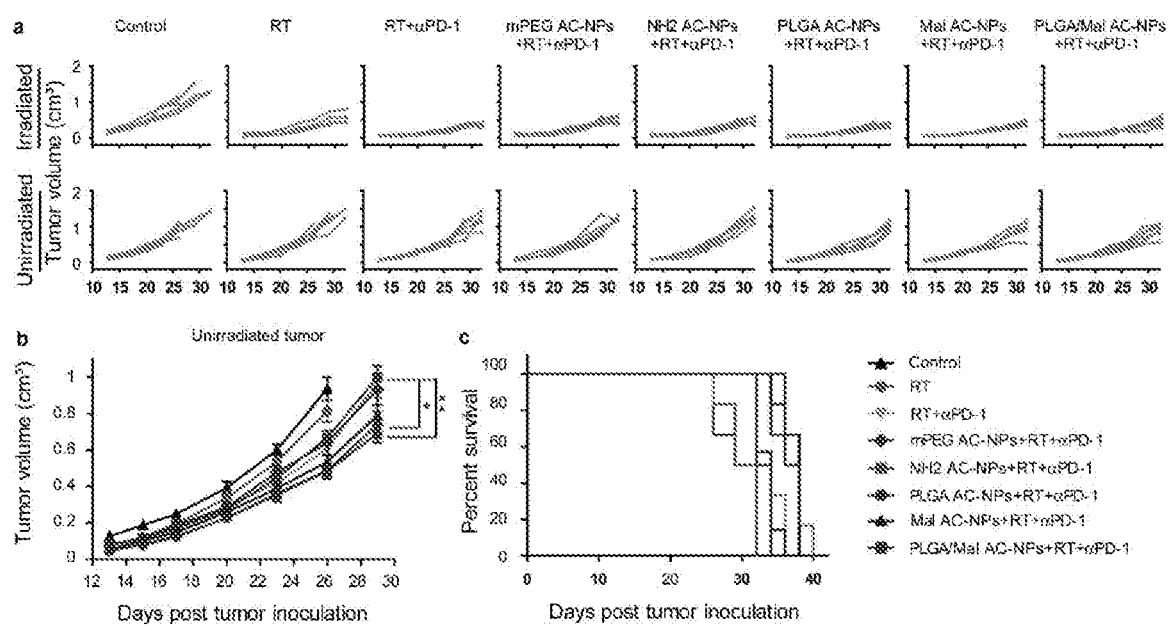
FIGS. 24(a)-24(c) show that AC-NPs can improve immunotherapy and the abscopal effect in 4T1 tumor model.

A syngeneic mouse model of melanoma was used to evaluate whether the AC-NPs can enhance the immune response in the context of checkpoint inhibitors. Mice bearing bilateral B16F10 melanoma flank tumors were given αPD-1 treatment. One of the tumors was irradiated (primary) and then injected with either PBS or AC-NPs, while the other tumor was shielded from radiation (secondary) (FIG. 2; FIG. 15(a)). The immunotherapeutic efficacy and induction of the abscopal effect were assessed by measuring tumor growths of the primary and secondary tumors. The PLGA and Mal AC-NPs were able to significantly enhance the therapeutic efficacy and the abscopal effect, eliciting the most robust therapeutic response across all treatment groups (FIGS. 11(a) and 11(b)). The greater therapeutic efficacy also translated into improved survival (FIG. 11(c)). The RT+αPD-1+PLGA AC-NP treatment strategy yielded a complete response rate (CRR) of 20%. When these animals were re-challenged with 100,000 B16F10 cells (higher tumor burden than initial experiment) three months later, they successfully rejected tumor growth (FIG. 25), suggesting that this treatment strategy is capable of supporting a durable anti-tumor immune response. In contrast, mPEG and $NH_2$ AC-NPs did not enhance the efficacy of RT+αPD-1. It's important to note that the injection of PLGA AC-NP into the unirradiated tumor (secondary) did not enhance immunotherapy response (FIG. 11(a)). Thus, the data demonstrated that AC-NPs (PLGA and Mal) can improve immunotherapy responses and mediate the abscopal effect. The immunotherapy responses were also observed in 4T1 tumor model (FIGS. 24(a)-24(b)).

Figure 2:
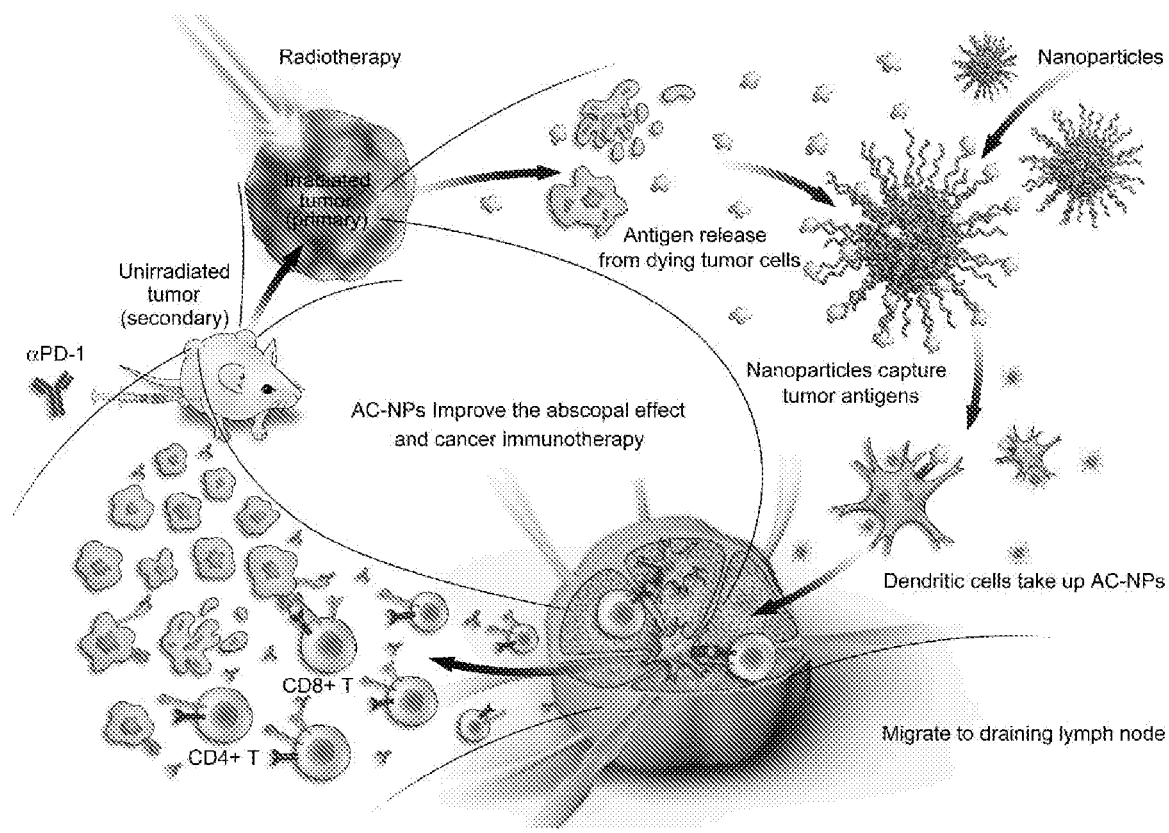
FIG. 2 depicts utilizing antigen-capturing nanoparticles (AC-NPs) for use in cancer immunotherapy. Following radiotherapy, AC-NPs bind to tumor antigens and enhance their presentation to dendritic cells. The enhanced antigen-presentation and immune activation is synergistic with αPD-1 treatment.
Figures 12A, 12B, 12C, 12D:
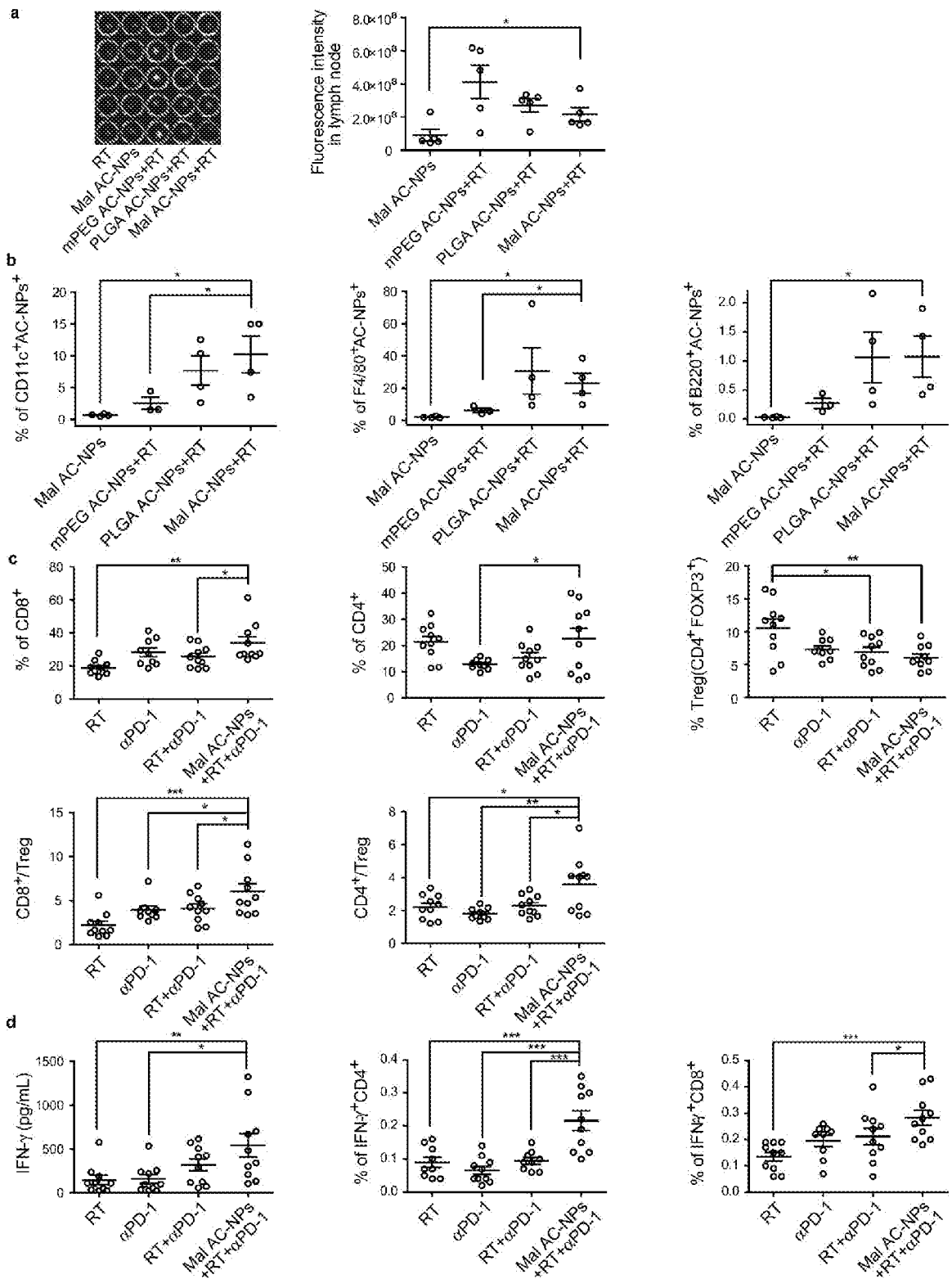
FIGS. 12(a)-12(d) show C-NPs enhance antigen presentation and increase immune activation.
Figures 16A, 16B, 16C:
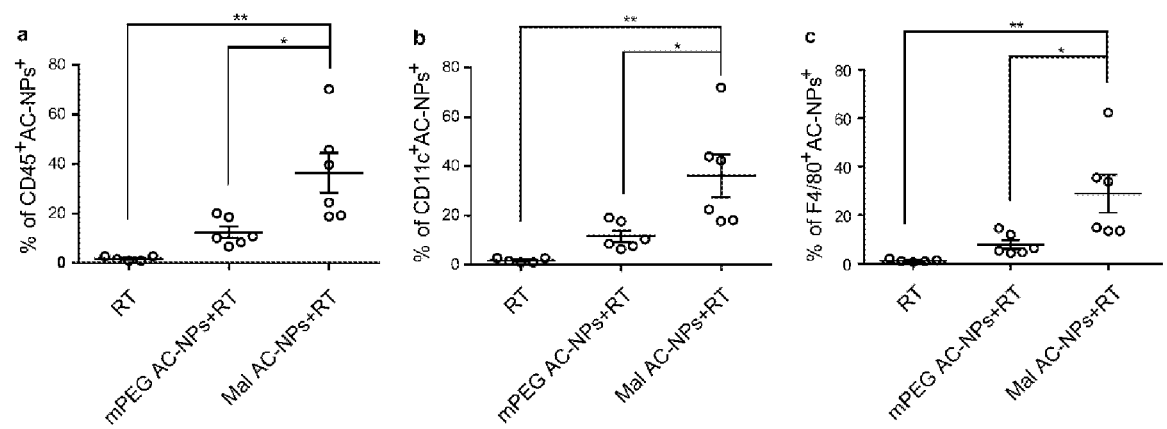
FIGS. 16(a)-16(c) show AC-NP accumulation in antigen presenting cells in the primary irradiated tumor following radiotherapy. Flow cytometric analysis demonstrated efficient uptake of fluorescently labeled Mal AC-NPs in hematopoietic cells (CD45$^+$), dendritic cells (CD11c$^+$) and macrophages (F4/80$^+$) (n=6). Statistical significance was assessed using a one-way analysis of variance (ANOVA) with Tukey's post-test. Data represent mean±standard error of the mean (SEM). P value: *, P<0.05; , P<0.01; * P<0.005.

The mechanism by which AC-NPs enhance the efficacy of cancer immunotherapy was investigated. As illustrated in FIG. 2, successful immunotherapeutic tumor response requires uptake and presentation of cancer antigens by APCs and elicitation of anti-tumor cellular immunity. To confirm that AC-NPs are capable of delivering cancer derived proteins to APCs, rhodamine-labeled AC-NPs were injected intratumorally and lymphatic drainage and distribution among lymph node resident dendritic cells, macrophages, and B-cells was studied following radiotherapy. The AC-NPs injected into irradiated tumors readily accumulate in the sentinel lymph node near the tumor 16 hours post administration, whereas Mal AC-NPs injected into unirradiated tumor did not accumulate in the tumor draining lymph nodes (FIG. 12(a)). Without being bound by theory, it is believed that nanoparticle accumulation is associated with immune activation. Importantly, PLGA and Mal AC-NPs accumulate at higher rates in professional antigen presenting cells, e.g., $CD11c^+$ cells (dendritic cells) and $F4/80^+$ cells (macrophages) when compared to mPEG AC-NPs. Additionally, a trend in the data suggests there is preferential uptake of PLGA and Mal AC-NPs by B-cells ($B220^+$) as well (FIG. 12(b)). In addition to lymph node resident APCs, AC-NPs were also found to accumulate in APCs present in the irradiated tumor (FIGS. 16(a)-16(c)). The data strongly indicate that AC-NPs have high recognition capacity by immune system, and can facilitate the delivery of TDPAs to APCs.

Figure 17:
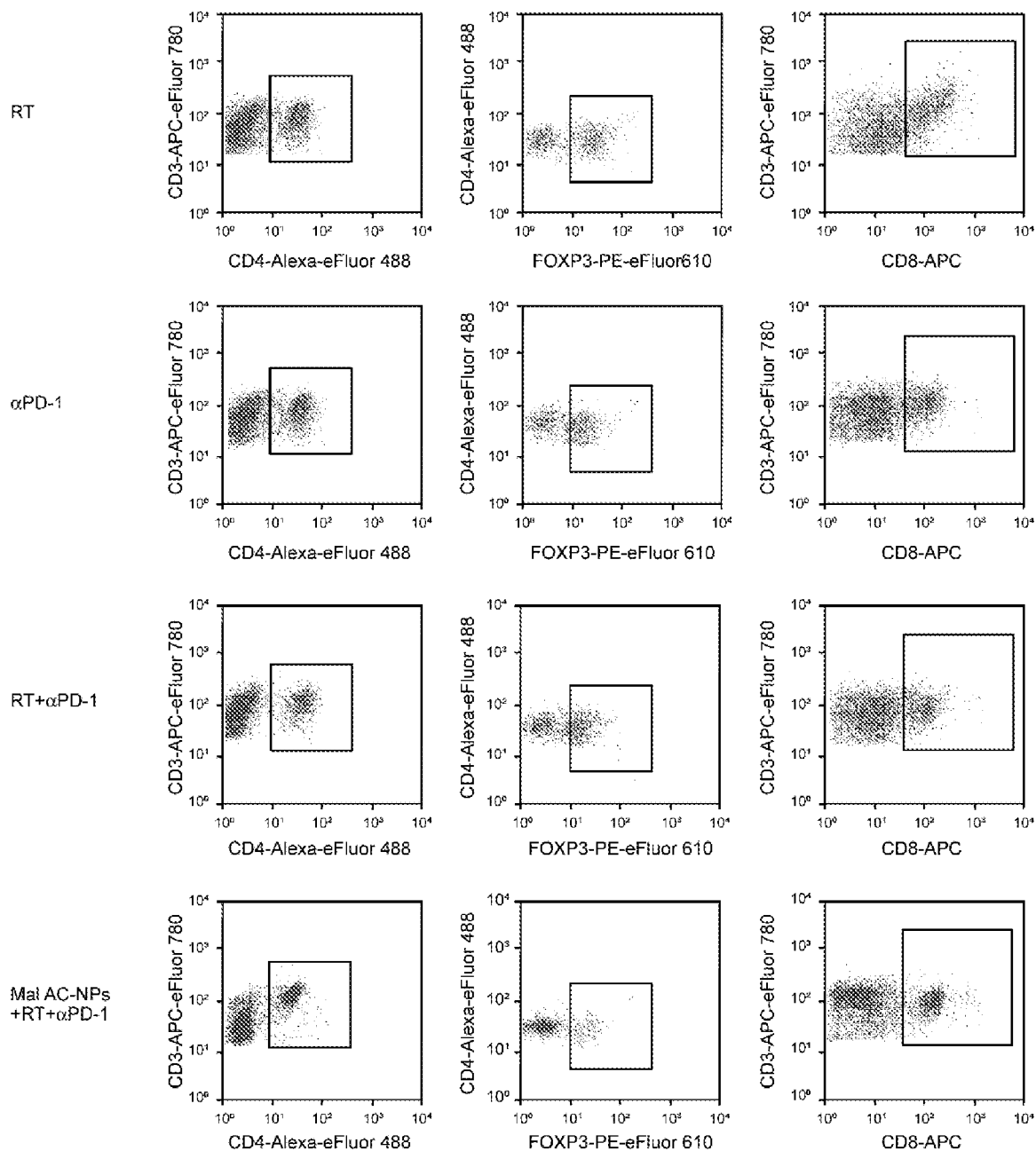
FIG. 17 shows representative flow plots and gating used to quantify changes in the relative abundance of T cell subpopulations in un-irradiated secondary tumors following treatment.
Figure 18:
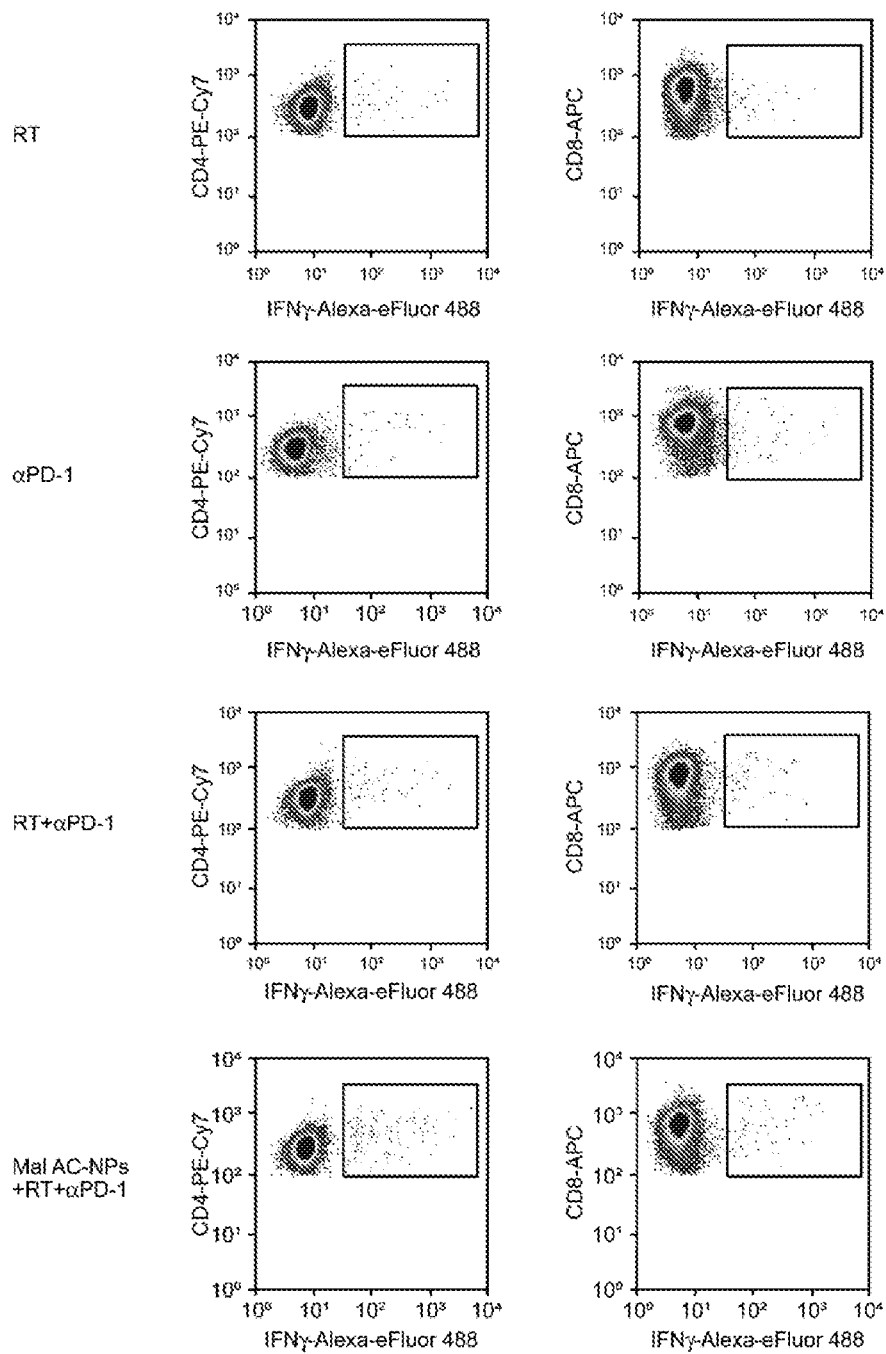
FIG. 18 shows representative flow plots used to evaluate frequency of IFN-γ producing T cells taken from spleens of animals treated with AC-NPs and subsequently stimulated ex vivo with cancer derived antigens.
Figure 19:
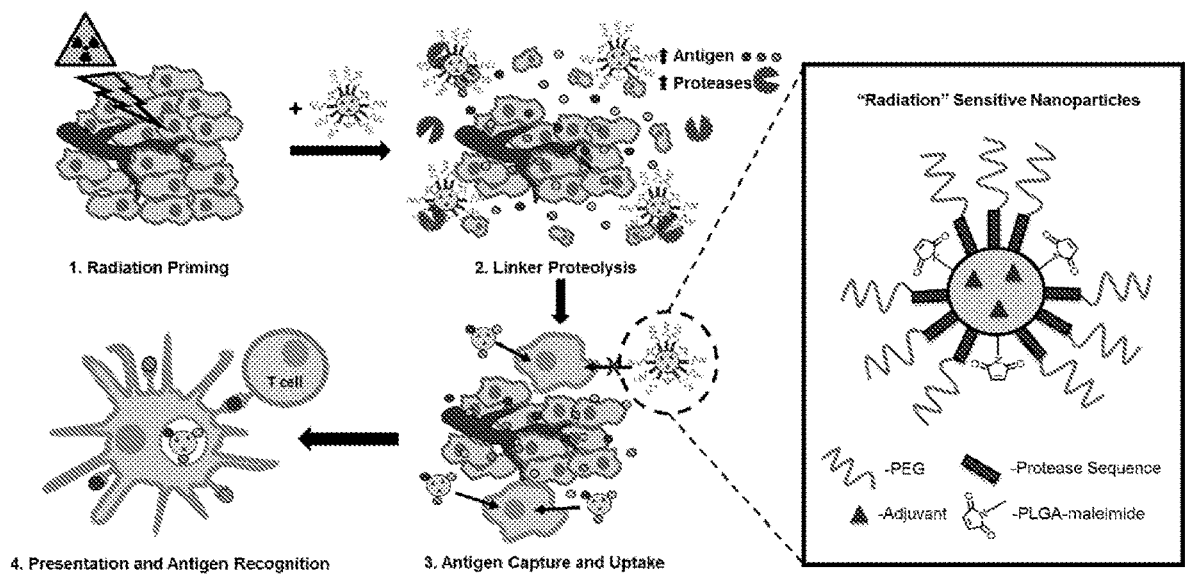
FIG. 19 shows the general concept of protease sensitive AC-NPs. The box on the right shows the nanoparticle structure displaying the four features described above. PLGA-maleimide can be replaced with PLGA. Step 1 depicts radiation priming the tumor to leach antigens and increase protease activity. Step 2 depicts following nanoparticle accumulation, the increased protease activity in the tumor microenvironment cleaves the sensitive protease sequences to remove the protective PEG layer. Step 3 depicts the exposed nanoparticle core and capturing moieties can adsorb leached antigens and then be phagocytosed by antigen presenting cells in the tumor bed. Nanoparticles that were not sufficiently proteolyzed will not capture antigen or be proteolyzed. Step 4 depicts phagocytosis of the AC-NP loaded with adjuvant and antigens will provide immune stimulation and antigen presentation. These cells can then stimulate the necessary T cells to mount an immune response against the tumor.
Figure 20:
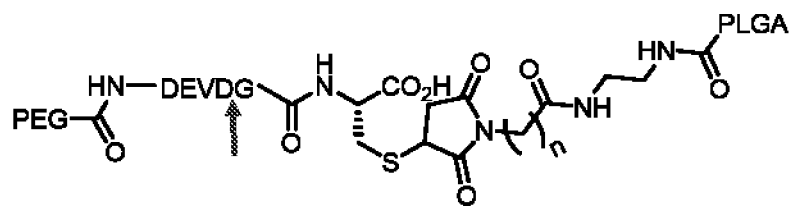
FIG. 20 shows the structure of protease sensitive polymers. Three peptide sequences are shown that correspond to proteases whose activity increases within the tumor microenvironment after radiotherapy. The protease cleavage site is denoted in red. The sequences were adapted from literature reports of cleavage sequences.
Figure 20:
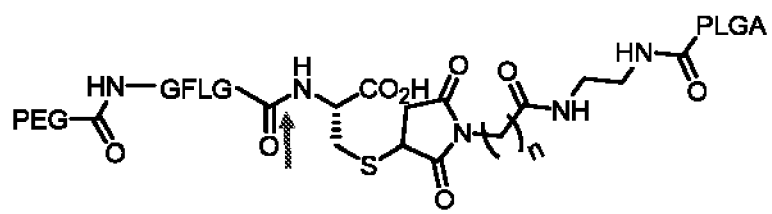
Figure 20:
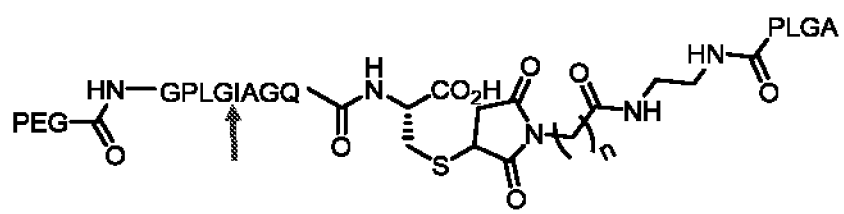
Figure 21:
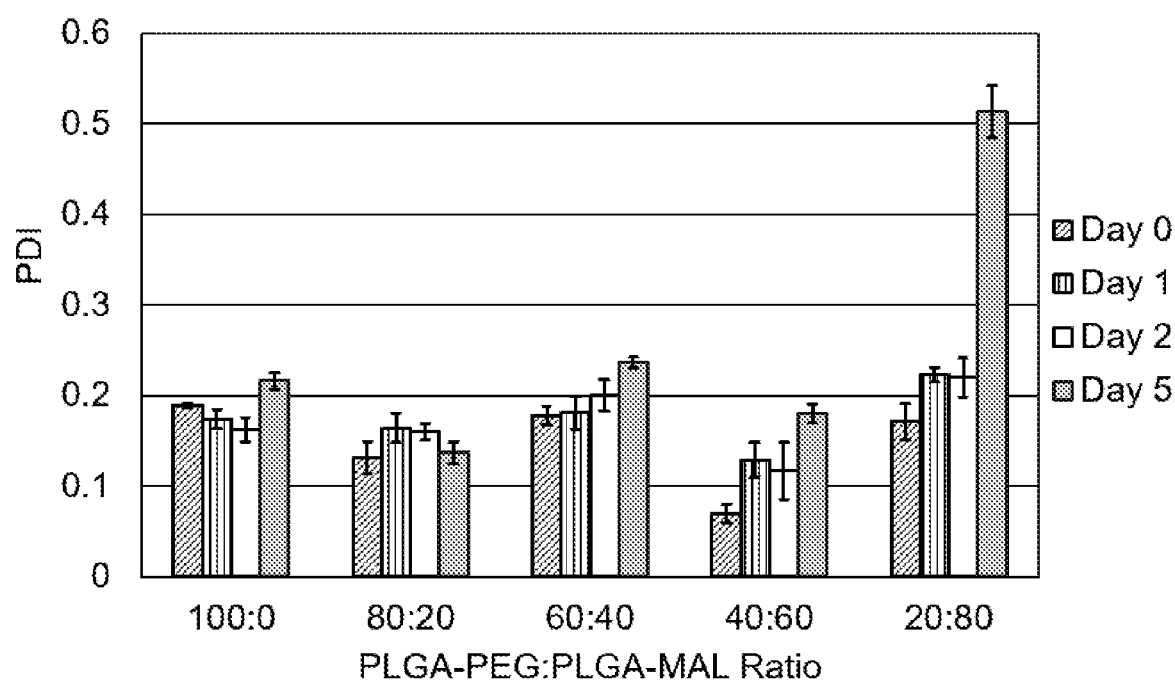
FIG. 21 shows the formulation stability of PLGA-PEG & PLGA-Maleimide.

APCs play a pivotal role in initiating a successful adaptive immune response by processing foreign antigens and presenting peptide fragments to naive T cells. Following antigen presentation, naïve $CD4^+$ and $CD8^+$ T cells become activated, experience clonal expansion and gain helper functions (e.g., cytokine secretion) or cytolytic capability. To determine whether the accumulation of AC-NPs carrying TDPAs would translate to successful T cell activation and expansion, the relative abundance of tumor infiltrating T cells was assessed in the untreated secondary tumors of animals 16 days following radiotherapy. The animals treated with Mal AC-NPs have more tumor infiltrating $CD4^+$ T cells when compared to mice that did not receive AC-NP treatment (FIG. 12(c); FIG. 17). On the other hand, the abundance of $CD4^+FOXP3^+$ regulatory T cells ($T_{reg}$), an immune suppressive T cell population that dampens antitumor immune response, substantially decreased when mice received combined immunotherapy, AC-NP, and radiotherapy (FIG. 12(c); FIG. 17). Overall, addition of AC-NPs in the therapeutic regimen significantly increased the ratios of tumor infiltrating $CD8^+$ $T/T_{reg}$ and $CD4^+$ $T/T_{reg}$ (FIG. 12(c)), implying increased anti-tumor cellular immunity in the tumor microenvironment. To further address whether AC-NPs are capable of eliciting systemic T cell activation, an assessment of the ex vivo production of antitumor cytokine interferon-γ (IFN-γ) (DeMuth, P. C. et al., Nat. Biotechnol. 31, 1082-1085 (2013)) by splenocytes harvested from mice that received different immunotherapy regimens was undertaken. The Mal AC-NPs induced the highest level of IFN-γ secretion following stimulation (FIG. 12(d)). Consistent with this observation, the Mal AC-NP treatment arm also contained the highest percentage of IFN-γ secreting $CD4^+$ T cells, indicating a more robust tumor specific systemic immune response (FIG. 12(d); FIG. 18). The results demonstrated that AC-NPs in combination with radiotherapy and immune checkpoint inhibition substantially increase antitumor $CD8^+$ and $CD4^+$ effector T cells both in quantity and quality.

Figure 25:
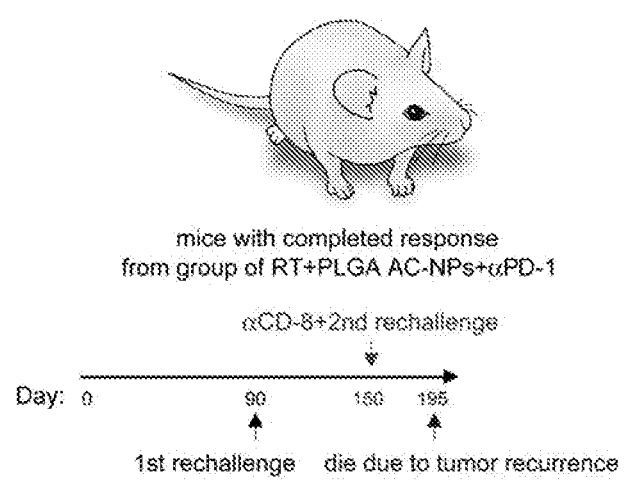
FIG. 25 shows mice with complete responses in B16-F10 tumor model were rechallenged with B16-F10 tumors. Time line starts from first tumor inoculation (day 0). Recurrence occurred only after anti-CD8 depletion and second rechallenge.

To confirm that the improved immunotherapeutic response and abscopal effect is due to AC-NP administration, the effect of direct administration of AC-NPs coated with TDPA to tumor bearing mice receiving αPD-1 immunotherapy treatment (FIG. 15(b)) was examined. Consistent with the in vivo AC-NP administration data, it was found that both Mal AC-NPs and PLGA AC-NPs significantly delayed tumor growth (FIGS. 13(a) and 13(b)) and increased survival time (FIG. 13(c)). In the mice that had complete responses, tumor rejection upon re-challenge was observed (FIG. 25).

As a secondary effect to radiotherapy, the abscopal effect promotes whole body, tumor rejection even at distal metastatic sites that received no radiation. The immune system appears to potentiate this powerful effect. In theory, radioablation causes tumors to leach tumor-associated antigens (TAAs) that prime the immune system to mount an antitumor response. However, examples and strategies to promote the abscopal effect remain rare.

The primary hurdle to an effective abscopal effect is the limited uptake and presentation of secreted TAAs after radioablation. The synthesis of the first antigen capturing nanoparticles (AC-NPs) is described above. These particles are functionalized with moieties that adsorb secreted TAAs after radiotherapy. AC-NPs administered to the primary tumor post-irradiation significantly promoted an anti-tumor response against a secondary, unirradiated tumor. The first generation of AC-NPs were composed of PLGA-PEG functionalized with antigen capturing moieties at the terminal end of the PEG block. Although PEG greatly increases the particle stability and circulation time in vivo, it can also detrimentally block protein (antigen) presentation and particle phagocytosis. Furthermore, the freely exposed antigen capturing functionalities could sequester non-immunogenic self antigens before migration to the tumor site or radioablation.

Stimuli sensitive AC-NPs respond to increased proteases activity (Caspase 3, Cathepsin B, and MMP2) within the tumor microenvironment after radiotherapy. In an embodiment, the antigen capturing moieties (maleimide or bare PLGA) are buried within the nanoparticle core and protected from premature protein adsorption and phagocytosis via a PEG corona. After radiation treatment, the increased protease activity in the tumor micro-environment (TME) cleaves the protective PEG layer, exposes the antigen capturing moieties, and improves uptake by recruited immune cells. To impart this action, the PLGA and PEG block co-polymer domains are linked via protease sensitive peptides. The optimal formulations that promote particle stability while blocking particle phagocytosis were investigated.

In an embodiment, the nanoparticles described herein comprise a PEG corona. The PEG corona may block premature and nonspecific protein adsorption before radiotherapy and accumulation in the tumor. The PEG corona may also prevent phagocytosis before radiotherapy and accumulation in the tumor.

In another embodiment, the nanoparticles described herein comprise a protease sensitive linker. The protease sensitive linker may form a linkage between poly-lactic-glycolic acid core (PLGA) and PEG corona. The protease sensitive linker may also provide a stimuli sensitive moiety that cleaves to remove PEG when protease activity in the tumor microenvironment increases. The protease sensitive linker may have a C-terminal cysteine residue on the peptide which allows for ligation to PLGA-maleimide via a thiol Michael reaction.

In another embodiment, the nanoparticles described herein comprise a particle core. The particle core may be composed of PLGA or PLGA-maleimide. The particle core may provide either functional groups (such as with maleimide) or a hydrophobic surface (such as with unmodified PLGA) to capture proteins via covalent or hydrophobic-hydrophobic interactions after PEG removal by proteases. The protease sensitive linker may encapsulate adjuvants such as lipopolysaccharide, monophosphoryl lipid a, imiquimod, resiquimod, thiolated nucleic acids [CpG, ssRNA], and DMXAA.

In another embodiment, the nanoparticle described herein comprise adjuvants loaded in the core. The adjuvant, examples of which are listed above, may increase the immune response by antigen presenting cells after PEG cleavage and phagocytosis.

I. Definitions

As used herein, "abscopal effect" refers to a phenomenon in the treatment of cancer where localized treatment of a tumor effects not only the treated tumor, but also tumors outside the scope of the localized treatment.

As used herein, the phrase "potentiating the abscopal effect" refers to an increase in the abscopal effect of 1%, 2%, 3%, 4%, 5,%, 10%, 20%, 30%, 40%, 50%, 60%, 70%, 80%, 90%, 95%, 99%, or 100%, following administration of antigen-capturing nanoparticles, relative to the abscopal effect seen in the absence of the antigen-capturing nanoparticles.

As used herein, the term "liposome" refers to an artificial microscopic vesicle consisting of an aqueous core enclosed in one or more phospholipid layers, used to convey vaccines, drugs, enzymes, or other substances to target cells or organs.

As used herein, the term "non-covalent" refers to the interactions between two or more species wherein the interactions are, for example, hydrogen bonds, Coulombic interactions, ionic bonds, van der Waals forces, and/or hydrophobic interactions.

The term "covalently bound" or "covalently linked" refers to a chemical bond formed by sharing of one or more pairs of electrons.

The term "ionic bond" refers to the formation of ions by transfer of one or more electrons from one atom to another, thus generating two oppositely charged ions.

As used herein, the "contacting" refers to reagents in close proximity so that a reaction may occur.

The term "linker" as used herein means a chemical moiety comprising a chain of atoms that covalently attaches the core of a nanoparticle to other chemical moieties. The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including, but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

As used herein, the term "checkpoint inhibitor" or "immune checkpoint inhibitor" is any molecule that directly or indirectly inhibits, partially or completely, an immune checkpoint pathway. Without wishing to be bound by any particular theory, it is generally thought that immune checkpoint pathways function to turn on or off aspects of the immune system, particularly T cells. Following activation of a T cell, a number of inhibitory receptors can be upregulated and present on the surface of the T cell in order to suppress the immune response at the appropriate time. In the case of persistent immune stimulation, such as with chronic viral infection, for example, immune checkpoint pathways can suppress the immune response and lead to immune exhaustion. Aspects of the disclosure are related to the observation that inhibiting such immune checkpoint pathways and administering synthetic nanocarrier compositions comprising antigens and immunostimulators, can result in the generation of enhanced immune responses to the antigen and/or a reduction in immunosuppressive immune responses against the antigen. Examples of immune checkpoint pathways include, without limitation, PD-1/PD-L1, CTLA4/B7-1, TIM-3, LAG3, By-He, H4, HAVCR2, ID01, CD276 and VTCN1. In the instance of the PD-1/PD-L1 immune checkpoint pathway, an inhibitor may bind to PD-1 or to PD-L1 and prevent interaction between the receptor and ligand. Therefore, the inhibitor may be an anti-PD-1 antibody or anti-PD-L1 antibody. Similarly, in the instance of the CTLA4/B7-1 immune checkpoint pathway, an inhibitor may bind to CTLA4 or to B7-1 and prevent interaction between the receptor and ligand. Non-limiting examples of immune checkpoint inhibitors include fully human monoclonal antibodies, such as BMS-936558/MDX-1106, BMS-936559/MDX-1105, ipilimumab/Yervoy, and tremelimumab; humanized antibodies, such as CT-011 and MK-3475; and fusion proteins, such as AMP-224.

As used herein, the terms "capture" or "captured" refers to the binding of a nanoparticle to an antigen.

As used herein, the term "lipid" refers to a member of a group of organic compounds that has lipophilic or amphipathic properties, including, but not limited to, fats, fatty oils, essential oils, waxes, steroids, sterols, phospholipids, glycolipids, sulpholipids, aminolipids, chromolipids (lipochromes), and fatty acids. The term "lipid" encompasses both naturally occurring and synthetically produced lipids. "Lipophilic" refers to those organic compounds that dissolve in fats, oils, lipids, and non-polar solvents, such as organic solvents. Lipophilic compounds are sparingly soluble or insoluble in water. Thus, lipophilic compounds are hydrophobic. Amphipathic lipids, also referred to herein as "amphiphilic lipids" refer to a lipid molecule having both hydrophilic and hydrophobic characteristics. The hydrophobic group of an amphipathic lipid, as described in more detail immediately herein below, can be a long chain hydrocarbon group. The hydrophilic group of an amphipathic lipid can include a charged group, e.g., an anionic or a cationic group, or a polar, uncharged group. Amphipathic lipids can have multiple hydrophobic groups, multiple hydrophilic groups, and combinations thereof. Because of the presence of both a hydrophobic group and a hydrophilic group, amphipathic lipids can be soluble in water, and to some extent, in organic solvents.

The term "hydrophobic" is a physical property of a molecule that is repelled from a mass of water and can be referred to as "nonpolar," or "apolar," all of which are terms that can be used interchangeably with "hydrophobic." Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s).

As used herein, "hydrophilic" is a physical property of a molecule that is capable of hydrogen bonding with a water molecule and is soluble in water and other polar solvents. The terms "hydrophilic" and "polar" can be used interchangeably. Hydrophilic characteristics derive from the presence of polar or charged groups, such as carbohydrates, phosphate, carboxylic, sulfato, amino, sulfhydryl, nitro, hydroxy and other like groups.

Examples of amphipathic compounds include, but are not limited to, phospholipids, aminolipids and sphingolipids. Representative examples of phospholipids include, but are not limited to, phosphatidylcholine, phosphatidyletha-nolamine, phosphatidylserine, phosphatidylinositol, phosphatidic acid, palmitoy-loleoyl phosphatidylcholine, lyso-phosphatidylcholine, lysophosphatidylethanolamine, dipalmitoyl-phosphatidylcholine, dioleoylphosphatidylcholine, distearoylphosphatidylcholine, dioleoyl phosphatidic acid, and dilinoleoylphosphati-dylcholine. Other compounds lacking in phosphorus, such as sphingolipid, glycosphingolipid families, diacylglycerols and β-acyloxyacids, also are within the group designated as amphipathic lipids.

As used herein, the term "cationic lipid" encompasses any of a number of lipid species that carry a net positive charge at physiological pH, which can be determined using any method known to one of skill in the art. These include, but are not limited to, N-methyl-N-(2-(argin-oylamino)ethyl)-N,N-Di octadecyl aminium chloride or di stearoyl arginyl ammonium chloride] (DSAA), N,N-dimyristoyl-N-methyl-N-2 [N'(N$^6$-guanidino-L-lysinyl)] aminoethyl ammonium chloride (DMGLA), N,N-dimyris-toyl-N-methyl-N-2[N$^2$-guanidino-L-lysinyl]aminoethyl ammonium chloride, N,N-dimyristoyl-N-methyl-N-2 [N'(N2,N6-di-guanidino-L-lysinyl)] aminoethyl ammonium chloride, and N,N-di-stearoyl-N-methyl-N-2[N' (N6-guanidino-L-lysinyl)] aminoethyl ammonium chloride (DS-GLA). Other non-limiting examples of cationic lipids that can be present in the liposome or lipid bilayer of the presently disclosed delivery system complexes include N,N-dioleyl-N, N-dimethylammonium chloride (DODAC); N-(2,3-dioleoyloxy)propyl)-N,N,N-trimethylammonium chloride (DOTAP); N-(2,3-di-oleyloxy)propyl)-N,N,N-trimethylammonium chloride (DOTMA) or other N (N,N-1-dialkoxy)-alkyl-N,N,N-tri-substituted ammonium surfactants; N,N-distearyl-N,N-dimethylammoniumbromide (DDAB); 3-(N(N',N' dimethylaminoethane)carbamoyl) cholesterol (DC-Chol) and N-(1,2-dimyristyloxyprop-3-yl)-N,N-dimethyl-N-hydroxyethyl ammonium bromide (DMRIE); 1,3-dioleoyl-3-trimethylammonium-propane,N-(1-(2,3-dioleyloxy)propyl)-N-(2-(sperminecarboxamido)ethyl)-N,N-dimethyl-lammoniumtrif-luoro acetate (DOSPA); GAP-DLRIE; DMDHP; 3-β[$^4$N($^1$N, N-diguanidinospermidine) carbamoyl] cholesterol (BGSC); 3-β[N,N-diguanidinoethyl-aminoethane)-carbamoyl] cholesterol (BGTC); N,N$^1$,N$^2$,N$^3$ Tetra-methyltetrapalmityl-spermine (cellfectin); N-t-butyl-N'-tetradecyl-3-tetradecyl-aminopropion-amidine (CLONfectin); dimethyldioctadecyl ammonium bromide (DDAB); 1,3-dioleoyloxy-2-(6-car-box-yspermy1)-propyl amide (DOSPER); 4-(2,3-bis-palmi-toy-loxy-propy1)-1-methy1-1H-imidazole (DPIM) N,N,N', N'-tet-ramethyl-N,N'-bis(2-hydroxyethyl)-2,3 dioleoyloxy-1,4-butanediammonium iodide) (Tfx-50); 1,2 dioleoyl-3-(4'-trimethylammonio) butanol-sn-glycerol (DOBT) or cholesteryl (4' trimethylammonia) butanoate (ChOTB) where the trimethylammonium group is connected via a butanol spacer arm to either the double chain (for DOTB) or choles-teryl group (for ChOTB); DL-1,2-dioleoyl-3-dimeth-ylami-nopropy1-β-hydroxyethylammonium (DORI) or DL-1,2-O-dioleoyl-3-dimethylaminopropy1-β-hydroxyeth-ylammonium (DORIE); 1,2-dioleoyl-3-succinyl-sn-glycerol choline ester (DOSC); cholesteryl hemisuccinate ester (ChOSC); lipopolyamines such as dioctadecylamidoglycyl-spermine (DOGS) and dipalmitoyl phosphatidylethanolam-ylspermine (DPPES); cholesteryl-3-β-carboxyl-amido-ethylenetrimethylammoniumiodide; 1-dimethylamino-3-trimethylammonio-DL-2-propyl-cholesteryl carboxylate iodide; cholesteryl-3-β-carboxyamidoethyleneamine; cholesteryl-3-β-oxysuccinamido-ethylenetrimethylammonium iodide; 1-dimethylamino-3-trimethylammonio-DL-2-propyl-cholesteryl-3-β-oxysuccinateiodide; 2-(2-trimethylammonio)-ethylmethylaminoethyl-cholesteryl-3-β-oxysuccinate iodide; and 3-β-N-(polyethyleneimine)-carbamoylcholesterol.

The term "target" as used herein indicates a biological system of interest including unicellular or pluricellular living organisms or any portion thereof, and include in vitro or in vivo biological systems or any portion thereof.

The term "polymer" as used herein indicates a large molecule composed of repeating structural units typically connected by covalent chemical bonds. A suitable polymer may be linear and/or branched, and can take the form of a homopolymer or a co-polymer. If a co-polymer is used, the co-polymer may be a random co-polymer or a branched co-polymer. Exemplary polymers comprise water-dispersible and in particular water soluble polymers. For example, suitable polymers include, but are not limited to polysaccharides, polyesters, polyamides, polyethers, polycarbonates, polyacrylates, polyethylenimines and derivatives thereof. A derivative of a polymer may be either commercially available or it can be prepared as described herein. For therapeutic and/or pharmaceutical uses and applications, the polymer should have a low toxicity profile and in particular that are not toxic or cytotoxic. In other words, the polymer should be biocompatible. For example, maleimide derivatized PLGA is a preferable polymer material.

As used herein, the term "nanoparticle" refers to particles of any shape having at least one dimension that is less than about 1000 nm. In some embodiments, nanoparticles have at least one dimension in the range of about 1 nm to about 1000 nm, including any integer value between 1 nm and 1000 nm (including about 1, 2, 5, 10, 20, 30, 40, 50, 60, 70, 80, 90, 100, 200, 500, and 1000). In certain embodiments, the nanoparticles have at least one dimension that is about 150 nm. Particle size can be determined using any method known in the art, including, but not limited to, sedimentation field flow fractionation, photon correlation spectroscopy, disk centrifugation, and dynamic light scattering.

As used herein, the term "alarmin" refers to any molecule released from a damaged or diseased cell that stimulates an immune response. Non-limiting examples of alarmins are heat-shock proteins, interleukin-1a, HMGB1, and nucleosomes.

The term "antigen" as used herein refers broadly to any antigen to which an individual can generate an immune response. "Antigen" as used herein refers broadly to molecules that contains at least one antigenic determinant to which the immune response may be directed. The immune response may be cell mediated or humoral or both.

As is well known in the art, an antigen may be protein in nature, carbohydrate in nature, lipid in nature, or nucleic acid in nature, or combinations of these biomolecules. An antigen may include non-natural molecules such as polymers and the like. Antigens include self antigens and foreign antigens such as antigens produced by another animal or antigens from an infectious agent. Infectious agent antigens may be bacterial, viral, fungal, protozoan, and the like.

The term "tumor antigen" as used herein refers to a protein which is present on tumor cells, and on normal cells during fetal life (onco-fetal antigen), after birth in selected organs, or on many normal cells, but at much lower concentration than on tumor cells. A variety of tumor antigens have been described. Non-limiting examples of tumor antigens are mucin such as MUC1 or the HER2 (neu) antigen.

As used herein, the phrase "antigen presenting cell" or "APC," has its art understood meaning referring to cells which process and present antigens to T-cells. Non-limiting examples of antigen cells include dendritic cells, macrophages and certain activated epithelial cells.

As used herein, the term "Cathepsin" or "Cathepsin family" refers to the family of proteases distinguished by their structure, catalytic mechanism, and which proteins they cleave. The Cathepsin family includes Cathepsin A, B, C, D, E, F, G, H, K, L1, L2, O, S, W, and Z.

A "Cathepsin cleavable peptide" is a peptide which is cleaved by a member of the Cathepsin family of enzymes.

As used herein, "MMP2" refers to the protein known as matrix metalloproteinase 2. It is an enzyme that in humans is encoded by the MMP2 gene.

As used herein, the term "Caspase" or "Caspase family" refers to a family of cysteine aspartic proteases. The Caspase family includes Caspase 1, 2, 3, 4, 5, 6, 7, 8, 9, 10, 11, 12, and 14.

By "therapeutically effective amount" or "dose" is meant the concentration of a delivery system or a bioactive compound comprised therein that is sufficient to elicit the desired therapeutic effect. Non-limiting examples of a therapeutically effective amount includes range between 50 μg to 1 g, 100 μg to 500 mg, 200 μg to 250 mg, 300 μg to 100 mg, 400 μg to 50 mg, or 500 μg to 1 mg.

As used herein, "effective amount" is an amount sufficient to effect beneficial or desired clinical or biochemical results. An effective amount can be administered one or more times.

As used herein, the phrase "at least partially necrotizing" refers to a group of cancer cells or tumor within which at least some of the cancer cells are dying and releasing antigens. "At least partially necrotizing" means the tumor has partially responded to therapy. This also includes tumors in the process of releasing antigens.

As used herein, the term "immune cell" refers to cells of the immune system that are involved in protecting the body. Non-limiting examples of immune cells are myeloid cells, lymphoid cells, dendritic cells, T-cells, B-cells, and natural killer cells.

As used herein, the term "adjuvant" refers to an additional compound added to the nanoparticle. Non-limiting examples of adjuvants are lipopolysaccharides, monophosphoryl lipid a, imiquimod, resiquimod, thiolated nucleic acids [CpG, ssRNA], and 5,6-dimethylxanthenone-4-acetic acid (DMXAA).

As used herein, the term "cleavage peptide" refers to a peptide that is capable of being cleaved by an enzyme. Non-limiting examples of enzymes that may cleave the peptide are Cathepsin, Cathepsin B, Caspase 3, and MMP2.

As used herein, the term "reactive group" is defined as a group that will bind to an antigen. The reactive group may bind to the antigen using a covalent bond or a non-covalent interaction, such as hydrophobic-hydrophobic or ionic interactions. Non-limiting examples of a reactive group include $NH_2$, maleimide COOH, —CHO, —NHS, —SH, -epoxy, -azide, -alkyne, —$NHNH_2$, —$Si(OCH_2CH_3)_3$, orthopyridyl disulfide, nitrophenyl carbonate, carbonyl imidazole, tosylate, mesylate, acrylate, and vinylsulfone.

As used herein, the term "PEG corona" refers to a PEG polymer which encapsulates at least a portion of the surface of the nanoparticle. The PEG corona comprises polyethyleneglycol (PEG) and is covalently linked to the core through a linker. The PEG corona may be designated as PEG" and has a molecular weight range of between 100 to 10,000 Da, 200 to 5,000 Da, 300 to 1,000 Da, or 400 to 700 Da.

As used herein, the term "surface" refers to the outside part or uppermost layer.

As used herein, the term "protease sensitive" refers to a protein sequence that may be cleaved by an enzyme. Non-limiting examples of protein sequences which may be protease sensitive include Gly-Phe-Leu-Gly, Gly-Pro-Leu-Gly-Ile-Ala-Gly-Gln, and Glu-Val-Asp-Gly. Non-limiting enzymes that may cleave such a protein sequence are Cathepsins, Caspases, and MMP2.

As used herein, the phrase "wherein at least one" refers to at least 10%, 20%, 30%, 40%, 50%, 60%, 70%, 80%, 90%, 95%, or 99% of the available J groups are bound to the PEP-PEG.

II. Nanoparticles and their Use

The nanoparticles described herein comprise a core, wherein said core comprises

Polymer-X-J, wherein,

X is PEG' or a linker; and

J is a reactive group, wherein at least a portion of said J is present on the surface of said core and at least one of said J present on the surface is covalently bound to PEP-PEG".

As in any embodiment above, a nanoparticle wherein said polymer is selected from the group consisting of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polyureas, polystyrenes, polyamines, and poly(lactic-co-glycolic acid) (PLGA).

As in any embodiment above, a nanoparticle wherein the polymer is PLGA.

As in any embodiment above, a nanoparticle wherein said linker comprises ethylenediamine.

As in any embodiment above, a nanoparticle wherein said reactive group is $NH_2$, maleimide, methoxy, COOH, —CHO, —NHS, —SH, -epoxy, -azide, -alkyne, —$NHNH_2$, —$Si(OCH_2CH_3)_3$, orthopyridyl disulfide, nitrophenyl carbonate, carbonyl imidazole, tosylate, mesylate, acrylate, or vinylsulfone.

As in any embodiment above, a nanoparticle wherein said reactive group is maleimide.

As in any embodiment above, a nanoparticle wherein PEP is a protein sequence.

As in any embodiment above, a nanoparticle wherein said protein sequence is a protease sensitive protein sequence.

As in any embodiment above, a nanoparticle wherein said protein sequence is capable of being cleaved by Caspase, Cathepsin, or MMP2.

As in any embodiment above, a nanoparticle wherein said protein sequence is selected from the group consisting of: Gly-Phe-Leu-Gly, Gly-Pro-Leu-Gly-Ile-Ala-Gly-Gln, and Glu-Val-Asp-Gly.

As in any embodiment above, a nanoparticle wherein said PEP has a molecular weight of between about 600 and 1200, 700 and 1100, or 800 and 1000.

As in any embodiment above, a nanoparticle capable of binding an antigen and enhancing an immune response to said antigen.

As in any embodiment above, a nanoparticle wherein said binding is a hydrophobic-hydrophobic interaction.

As in any embodiment above, a nanoparticle wherein said binding is an ionic interaction.

As in any embodiment above, a nanoparticle wherein said binding is a covalent interaction.

As in any embodiment above, a nanoparticle further comprising at least one antigen bound thereto, wherein said antigen is released from a necrotizing tumor.

As in any embodiment above, a nanoparticle wherein said core further comprises an adjuvant.

As in any embodiment above, a nanoparticle wherein said adjuvant is selected from the group consisting of lipopolysaccharides, monophosphoryl lipid a, imiquimod, resiquimod, thiolated nucleic acids, and DMXAA.

As in any embodiment above, wherein when Polymer-X-J is X=PEG', X is covalently bound to the polymer.

As in any embodiment above, wherein when Polymer-X-J is X-J=lethicin/DOTAP, X-J is bound to the polymer by hydrophobic-hydrophobic interactions.

A method of preparing any embodiment above, comprising contacting said reactive group on said core with PEP-PEG", wherein said nanoparticle is prepared.

The method as in any embodiment above, wherein said polymer core comprises PLGA.

The method as in any embodiment above, wherein said polymer core further comprises an adjuvant.

As in any embodiment above, a method of enhancing or inducing an immune response in a subject having cancer comprising:

administering to the subject a nanoparticle comprising:

a core, wherein said core comprises

Polymer-X-J, wherein,

X is PEG' or a linker; and

J is a reactive group capable of reacting with a thiol, wherein at least a portion of said J is present on the surface of said core and at least one of said J present on the surface is covalently bound to PEP-PEG", wherein said subject has undergone previous treatment for said cancer.

The method as in any embodiment above, wherein the previous treatment is selected from the group consisting of radiation, chemotherapy, cryotherapy, hyperthermia, and surgery.

The method as in any embodiment above, wherein said treatment is radiation.

The method as in any embodiment above, wherein said radiation occurs from about 6 hours to about 3 days, or from about 6 hours to about 2 days, or from about 6 hours to 1 day, or from about 6 hours to 18 hours, or from about 6 hours to about 12 hours prior to said administration of said nanoparticle.

The method as in any embodiment above, wherein said cancer is at least partially necrotizing.

The method as in any embodiment above, wherein said cancer is melanoma or breast cancer.

The method as in any embodiment above, wherein said nanoparticle binds at least one antigen released from said at least partially necrotizing cancer.

The method as in any embodiment above, wherein said nanoparticle binds at least 10 tumor antigens, wherein each antigen is released from said at least partially necrotizing cancer.

The method as in any embodiment above, wherein said antigens comprise anti-CTLA-4 or anti-PD-1.

The method as in any embodiment above, wherein said nanoparticle bound to at least one of said antigen is capable of recognition by an immune cell.

The method as in any embodiment above, wherein the immune cell is a dendritic cell.

The method as in any embodiment above, wherein said administering of said nanoparticle increases CD8+ T-cells.

The method as in any embodiment above, wherein said administering of said nanoparticle significantly increased the ratios of tumor infiltrating CD8$^+$ T/T$_{reg}$ cells.

The method as in any embodiment above, wherein said administering of said nanoparticle significantly increased the ratios of tumor infiltrating CD4$^+$ T/T$_{reg}$ cells.

The method as in any embodiment above, wherein said administering of said nanoparticle results in an enhanced level of IFN-γ secretion.

The method as in any embodiment above, wherein said administering of said nanoparticle results in an enhanced percentage of IFN-γ secreting CD4$^+$ T cells.

The method as in any embodiment above, wherein said nanoparticle is administered in a therapeutically effective amount.

The method as in any embodiment above, wherein said nanoparticle is administered via injection.

The method as in any embodiment above, wherein said injection is direct injection into the necrotizing cancer.

The method as in any embodiment above, further comprising administering an adjuvant.

The method as in any embodiment above, wherein said adjuvant is selected from the group consisting of lipopolysaccharides, monophosphoryl lipid a, imiquimod, resiquimod, thiolated nucleic acids, and DMXAA.

The method as in any embodiment above, wherein said cancer releases Cathepsin, Caspase, or MMP2.

The method as in any embodiment above, wherein said nanoparticle is administered in an amount between 10 μg to 1 g, or 20 μg to 500 mg, 30 μg to 100 mg, 40 μg to 50 mg, 50 μg to 10 mg, 100 μg to 1 mg, or 200 μg to 500 μg.

In an embodiment, a method of enhancing or inducing an immune response in a subject having cancer comprising:
administering to the subject a nanoparticle comprising:
a core, wherein said core comprises Polymer-X-J, wherein,
X is PEG and J is NH$_2$, maleimide, methoxy, —COOH, —CHO, —NHS, —SH, -epoxy, -azide, -alkyne, —NHNH$_2$, —Si(OCH$_2$CH$_3$)$_3$, orthopyridyl disulfide, nitrophenyl carbonate, carbonyl imidazole, tosylate, mesylate, acrylate, or vinylsulfone; or
X-J is lecithin/DOTAP or polyethylenimine (PEI),
wherein said subject has undergone previous treatment for said cancer.

The method as in any embodiment above, wherein when Polymer-X-J is X=PEG', X is covalently bound to the polymer.

The method as in any embodiment above, wherein when Polymer-X-J is X-J=lethicin/DOTAP, X-J is bound to the polymer by hydrophobic-hydrophobic interactions.

The method as in any embodiment above, wherein said polymer is selected from the group consisting of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polyureas, polystyrenes, polyamines, and poly(lactic-co-glycolic acid) (PLGA).

The method as in any embodiment above, wherein said polymer is PLGA. The method as in any embodiment above, wherein said nanoparticle binds at least one antigen released following said previous treatment.

The method as in any embodiment above, wherein said nanoparticle binds to at least 10 tumor antigens.

The method as in any embodiment above, wherein said antigens comprise anti-CTLA-4 or anti-PD-1.

The method as in any embodiment above, wherein said nanoparticle has a molecular weight of between 17,000-63,400 Da.

The method as in any embodiment above, wherein said nanoparticle has a particle size of between 50-500 nm.

The method as in any embodiment above, wherein said nanoparticle has a zeta potential of at least ±5 mV, ±10 mV, ±15 mV, ±20 mV, or ±25 mV.

A method for potentiating the abscopal effect in a subject undergoing therapy for cancer, comprising administering to said subject an effective amount of a nanoparticle from any embodiment above.

As in any embodiment above, a pharmaceutical composition comprising a nanoparticle in a pharmaceutically acceptable excipient.

As in any embodiment above, a pharmaceutical composition, wherein said pharmaceutical composition is a liquid suitable for injection.

As in any embodiment above, a pharmaceutical composition, wherein said pharmaceutical composition is a lyophilized powder.

In a preferred embodiment, the nanoparticle has a hydrophobic surface and is comprised of a biodegradable polymer. The nanoparticle is combined with tumor cells that are lethally irradiated. The nanoparticle's hydrophobic surface will adsorb the tumor antigens that are released from tumor cells. The nanoparticle/antigen complex is then injected as a vaccine for cancer immunotherapy. The nanoparticle complex may be given together with agents that enhance cancer immunotherapy, such as, but not limited to, inhibitors of CTLA-4 and/or PD-1.

In another preferred embodiment, the nanoparticle mentioned above is directly injected into a lethally irradiated tumor in vivo to enhance cancer immunotherapy.

In another preferred embodiment, the nanoparticle has surface functional groups such as, but not limited to, maleimide and/or thiol group that can react and bind to tumor antigens/proteins. The nanoparticle is combined with tumor cells that are lethally irradiated. The nanoparticle's hydrophobic surface will adsorb the tumor antigens that are released from tumor cells. The nanoparticle/antigen complex is then injected as a vaccine for cancer immunotherapy. The nanoparticle complex may be given together with agents that enhance cancer immunotherapy, such as, but not limited to, inhibitors of CTLA-4 and/or PD-1.

In another preferred embodiment, the nanoparticle mentioned above is directly injected into a lethally irradiated tumor in vivo to enhance cancer immunotherapy.

In certain embodiments, the tumor antigens are from tumor cells that are treated with radiotherapy. In some embodiments, the antigens may be from tumor cells that are treated with heat (hyperthermia and/or cold (cryotherapy) therapy. In certain embodiments, the tumor antigens are from tumor cells that are treated with drugs that can lead to cell death. In certain embodiments, the tumor antigens are from tumor cells that killed using physical forces/means.

In certain embodiments, an inventive particle is any entity having a greatest dimension (e.g., diameter) of less than 500 microns (μm). In some embodiments, inventive particles have a greatest dimension of less than 300 μm. In some embodiments, inventive particles have a greatest dimension of less than 200 μm. In some embodiments, inventive particles have a greatest dimension of less than 100 μm. In some embodiments, inventive particles have a greatest dimension of less than 75 μm. In some embodiments, inventive particles have a greatest dimension of less than 50 μm. In some embodiments, inventive particles have a greatest dimension of less than 10 μm. In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm.

In some embodiments, the particles are spheres, spheroids, flat, plate-shaped, cubes, cuboids, ovals, ellipses, cylinders, cones, or pyramids. In some embodiments, the particles are microparticles (e.g., microspheres). In some embodiments, the particles are nanoparticles (e.g., nanospheres).

In some embodiments, the particles are polymeric particles. In some embodiments, the particles are liposomes. In some embodiments, the particles are micelles. Particles can be solid or hollow. The particles can comprise one or more layers (e.g., nanoshells, nanorings). The particles can be coated. In certain embodiments, the particles include an outer lipid monolayer. In certain embodiments, the particles include an outer lipid bilayer. In certain embodiments, the particles include a polymeric outer layer.

Any of the above embodiments, may also include a targeting agent (e.g., aptamers, antibodies, antibody fragments, etc.) on the surface of the particle. In general, the cell to be targeted by the inventive particle includes a target which is specifically bound by the targeting agent. The agents are able to be delivered to the particular targeted organ, tissue, cell, extracellular matrix, extracellular compartment, and/or intracellular compartment once the targeting agent specifically binds to the target on the cell or intracellular compartment.

The whole particle or a portion of the inventive particle may be biodegradable. In certain embodiments, the entire particle is biodegradable. In other embodiments, only a portion of the particle is biodegradable (e.g., the outer layer of the particle). In general, a biodegradable substance is one that can be broken down under physiological conditions. In certain embodiments, the components of the inventive particles are biocompatible. That is, the materials used to prepare the particles do not lead to an adverse reaction when introduced into a living biological system.

In certain embodiments, the inventive particle includes a polymeric core. In certain embodiments, the polymer used in the particle comprises polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polyureas, polystyrenes, and/or polyamines. In certain embodiments, the polymer used in the particle is a polyester. In some embodiments, a polymeric matrix may comprise poly(lactic-co-glycolic acid) (PLGA), polyethyleneglycol (PEG), and/or copolymers thereof. In some embodiments, a polymeric matrix can comprise proteins, lipids, surfactants, carbohydrates, small molecules, and/or polynucleotides.

In some embodiments, particles can be non-polymeric particles (e.g., metal particles, quantum dots, ceramics, inorganic materials, bone, etc.).

According to the subject matter contained herein, any agents can be co-delivered with the antigen-capturing nanoparticles, including, for example, chemotherapeutic agents (e.g., anti-cancer agents), diagnostic agents (e.g., contrast agents; radionuclides; and fluorescent, luminescent, and magnetic moieties), immune modulators such as, but not limited to, imiquimod and TGF beta inhibitors, and/or nutraceutical agents (e.g., vitamins, minerals, etc.), radioisotope (e.g., a radiotherapeutic or radiodiagnostic agent).

Exemplary agents to be delivered in accordance with the subject matter contained herein include, but are not limited to, small molecules (imiquimod), nucleic acids (CpG), proteins, lipids, carbohydrates, hormones, metals, radioactive elements and compounds, drugs, vaccines, immunological agents, etc., and/or combinations thereof.

In another aspect, the subject matter contained herein provides methods of formulating and utilizing nanoparticles containing multiple (>10) tumor antigens for cancer immunotherapy. The subject matter contained herein also describes a method of personalized cancer immunotherapy. The proposed nanoparticles can bind/capture tumor antigens from individual patients and utilized as cancer immunotherapy agents/vaccines. The association of tumor antigens to nanoparticles can be achieved in a variety of different ways. Physical association may be covalent or non-covalent. A covalent association may or may not involve a linker moiety. The particle, antigen may be directly associated with one another, e.g., by one or more covalent bonds, or the association may be mediated by one or more linkers. In some embodiments, a linker is a cleavable linker. In some embodiments, a linker is an aliphatic or heteroaliphatic linker. In some embodiments, the linker is a polyalkyl linker. In certain embodiments, the linker is a polyether linker. In certain embodiments, the linker is a polyethylene linker. In certain specific embodiments, the linker is a polyethylene glycol (PEG) linker. For example, the chelator may be associated with the polymer of the particle through a PEG linker.

In some embodiments, particles in accordance with the subject matter contained herein may be used to treat, alleviate, ameliorate, relieve, delay onset of, inhibit progression of, reduce severity of, and/or reduce incidence of one or more symptoms or features of a disease, disorder, and/or condition. In some embodiments, inventive targeted particles may be used to treat cancer. In certain embodiments, inventive targeted particles may be used to treat a benign neoplasm. In certain embodiments, inventive targeted particles may be used to treat an inflammatory disease. In certain embodiments, inventive targeted particles may be used to treat an infectious disease. In certain embodiments, inventive targeted particles may be used to treat a cardiovascular disease (e.g., atherosclerosis). The compositions, according to the method of the subject matter contained herein, may be administered using any amount and any route of administration effective for treatment.

As in any embodiment above, a formulation of antigen capturing nanoparticles that is capable of binding/capturing >10 tumor antigens and the use of such nanoparticles for cancer immunotherapy.

As in any embodiment above, a formulation of antigen capturing nanoparticles wherein the drug delivery device is a particle. The formulation of antigen capturing nanoparticles wherein the drug delivery device is a liposome. The formulation of antigen capturing nanoparticles wherein the drug delivery device is a micelle. The formulation of antigen capturing nanoparticles wherein the device is a nanoparticle.

As in any embodiment above, a formulation of antigen capturing nanoparticles wherein the device is a microparticle.

As in any embodiment above, a formulation of antigen capturing nanoparticles wherein the particle surface is hydrophobic and the binding of antigens is from hydrophobic-hydrophobic interactions.

As in any embodiment above, a formulation of antigen capturing nanoparticles wherein the particle surface has a binding group such as, but not limited to, maleimide and/or thiol and these groups are used for binding the antigens to the nanoparticles.

As in any embodiment above, a particle wherein the tumor antigen is captured after radiation.

As in any embodiment above, a particle wherein the tumor antigen is captured after heat or cryotherapy.

As in any embodiment above, a particle wherein the tumor antigen is captured after cytotoxic therapy.

As in any embodiment above, a particle wherein said particle is comprised of biodegradable material.

As in any embodiment above, a particle wherein said particle is comprised of biocompatible material.

As in any embodiment above, a particle wherein the agent is delivered with the nanoparticle-antigen complex and the agent is a chemotherapeutic agent for cancer.

As in any embodiment above, a particle wherein the agent is delivered with the nanoparticle-antigen complex and the agent is a chemotherapeutic agent for treatment of an infectious disease.

As in any embodiment above, a particle wherein the agent is a chemotherapeutic agent for the treatment of an inflammatory disease.

As in any embodiment above, a particle wherein the agent is a chemotherapeutic agent for the treatment of an autoimmune disease.

As in any embodiment above, a particle wherein the agent is an immune modulator such as, but not limited to, imiquimod.

As in any embodiment above, a particle wherein the agent affects immune reaction pathways, such as, but not limited to, tgf-beta inhibitors.

As in any embodiment above, a particle further comprising a targeting moiety.

As in any embodiment above, a particle wherein the matrix comprises a natural or synthetic polymer.

As in any embodiment above, a particle wherein the matrix comprises a biodegradable polymer.

As in any embodiment above, a particle wherein the matrix comprises a biocompatible polymer.

As in any embodiment above, a particle wherein the matrix comprises a polymer selected from the group consisting of poly(lactic acid), derivatives of poly(lactic acid), PEGylated poly(lactic acid), poly(lactic-co-glycolic acid), derivatives of poly(lactic-co-glycolic acid), PEGylated poly(lactic-co-glycolic acid), poly(anhydrides), PEGylated poly(anhydrides), poly(ortho esters) derivatives of poly(ortho esters), PEGylated poly(ortho esters), poly(caprolactones), derivatives of poly(caprolactone), PEGylated poly(caprolactones), polylysine, derivatives of polylysine, PEGylated polylysine, poly(ethylene imine), derivatives of poly(ethylene imine), PEGylated poly(ethylene imine), poly(acrylic acid), derivatives of poly(acrylic acid), PEGylated poly(acrylic acid), poly(urethane), PEGylated poly(urethane), derivatives of poly(urethane), and combinations thereof.

As in any embodiment above, a particle wherein the matrix comprises a polymer selected from the group consisting of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, and combinations thereof.

As in any embodiment above, a particle wherein the greatest dimension of the particle ranges from approximately 1 nm to approximately 100 nm.

As in any embodiment above, a particle wherein the greatest dimension of the particle ranges from approximately 50 nm to approximately 100 nm.

As in any embodiment above, a particle wherein the greatest dimension of the particle ranges from approximately 50 nm to approximately 1000 nm.

As in any embodiment above, a particle that is injected as a vaccine.

As in any embodiment above, a particle that is injected into the tumor directly.

As in any embodiment above, a particle that is injected systemically.

As in any embodiment above, a formulation of antigen capturing nanoparticles that is capable of binding/capturing >10 tumor antigens and the use of such nanoparticles for cancer immunotherapy.

As in any embodiment above, a formulation of antigen capturing nanoparticles wherein the drug delivery device is a particle.

As in any embodiment above, a formulation of antigen capturing nanoparticles wherein the drug delivery device is a liposome.

As in any embodiment above, a formulation of antigen capturing nanoparticles wherein the drug delivery device is a micelle.

As in any embodiment above, a formulation of antigen capturing nanoparticles wherein the device is a nanoparticle.

As in any embodiment above, a formulation of antigen capturing nanoparticles wherein the device is a microparticle.

As in any embodiment above, a formulation of antigen capturing nanoparticles wherein the particle surface is hydrophobic and the binding of antigens is from hydrophobic-hydrophobic interactions.

As in any embodiment above, a formulation of antigen capturing nanoparticles, wherein the particle surface has a binding group such as, but not limited to, maleimide and/or thiol and these groups are used for binding of the antigens to the nanoparticles.

As in any embodiment above, a particle wherein the tumor antigen is captured after radiation.

As in any embodiment above, a particle wherein the tumor antigen is captured after heat or cryotherapy.

As in any embodiment above, a particle wherein the tumor antigen is captured after cytotoxic therapy.

III. Formulations

As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

As one of ordinary skill in the art would appreciate, a presently disclosed pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions or dispersions such as those described elsewhere herein and sterile powders for the extemporaneous preparation of sterile injectable solutions or dispersions. For intravenous administration, suitable carriers include physiological saline, bacteriostatic water, or phosphate buffered saline (PBS). The composition should be sterile and should be fluid to the extent that easy syringability exists. In some embodiments, the pharmaceutical compositions are stable under the conditions of manufacture and storage and should be preserved against the contaminating action of microorganisms, such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In some embodiments, isotonic agents, for example, sugars, polyalcohols, such as mannitol or sorbitol, or sodium chloride are included in the formulation. Prolonged absorption of the injectable formulation can be brought about by including in the formulation an agent that delays absorption, for example, aluminum monostearate and gelatin.

Sterile injectable solutions can be prepared by filter sterilization as described elsewhere herein. In certain embodiments, solutions for injection are free of endotoxin. Generally, dispersions are prepared by incorporating the delivery system complexes into a sterile vehicle which contains a basic dispersion medium and the required other ingredients from those enumerated above. In those embodiments in which sterile powders are used for the preparation of sterile injectable solutions, the solutions can be prepared by vacuum drying and freeze-drying which yields a powder of the active ingredient plus any additional desired ingredient from a previously sterile-filtered solution thereof.

Oral compositions generally include an inert diluent or an edible carrier. Oral compositions can be prepared using a fluid carrier for use as a mouthwash. Pharmaceutically compatible binding agents, and/or adjuvant materials can be included as part of the composition. The oral compositions can include a sweetening agent, such as sucrose or saccharin; or a flavoring agent, such as peppermint, methyl salicylate, or orange flavoring.

For administration by inhalation, the presently disclosed compositions can be delivered in the form of an aerosol spray from a pressured container or dispenser which contains a suitable propellant, e.g., a gas such as carbon dioxide, or a nebulizer. Liquid aerosols, dry powders, and the like, also can be used.

Systemic administration of the presently disclosed compositions also can be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical or cosmetic carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

By "therapeutic activity," when referring to a bioactive compound, is intended to mean that the molecule is able to elicit a desired pharmacological or physiological effect when administered to a subject in need thereof.

As used herein, the terms "treatment" or "prevention" refer to obtaining a desired pharmacologic and/or physiologic effect. The effect may be prophylactic in terms of completely or partially preventing a particular infection or disease or sign or symptom thereof and/or may be therapeutic in terms of a partial or complete cure of an infection or disease and/or adverse effect attributable to the infection or the disease. Accordingly, the method "prevents" (i.e., delays or inhibits) and/or "reduces" (i.e., decreases, slows, or ameliorates) the detrimental effects of a disease or disorder in the subject receiving the compositions of the invention. The subject may be any animal, including a mammal, such as a human, and including, but by no means limited to, domestic animals, such as feline or canine subjects, farm animals, such as, but not limited to, bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The disease or unwanted condition to be treated can encompass any type of condition or disease that can be treated therapeutically. In some embodiments, the disease or unwanted condition that is to be treated is a cancer. The term "cancer" encompasses any type of unregulated cellular growth and includes all forms of cancer. In some embodiments, the cancer to be treated is a metastatic cancer. Examples of cancer to be treated herein include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cell carcinoma, brain cancer, esophageal cancer, prostate cancer, vulval cancer, thyroid cancer, hepatic carcinoma, anal carcinoma, penile carcinoma, non-hodgkins lymphoma, hodgkin's lymphoma, as well as head and neck cancer.

In particular, the cancer may be resistant to known therapies. Methods to detect the inhibition of cancer growth or progression are known in the art and include, but are not limited to, measuring the size of the primary tumor to detect a reduction in its size, delayed appearance of secondary tumors, slowed development of secondary tumors, decreased occurrence of secondary tumors, and slowed or decreased severity of secondary effects of disease.

The following examples are offered by way of illustration and not by way of limitation.

EXAMPLES

Example 1: General Experimental Methods

Reagents

Methoxy poly(ethylene glycol)-b-poly(lactide-co-glycolide) (AK26), mPEG-PLGA (AK037; LA:GA=50:50 (w:w); $M_W$: ~25,000 Da), Poly(lactide-co-glycolide)-b-poly(ethylene glycol)-carboxylic acid endcap (AI076), Poly(lactide-co-glycolide)-b-poly(ethylene glycol)-amine endcap (AI058; $M_W$: ~17,000 Da), Poly(lactide-co-glycolide)-b-poly(ethylene glycol)-maleimide (AI052; LA:GA=75:25; $M_W$: ~63,400 Da), PLGA (poly(D,Llactide-co-glycolide)) with a 50:50 monomer ratio, acid-terminated (AP059; $M_W$: 45,000-55,000 Da), Poly(lactide-co-glycolide)-Rhodamine B (PLGA-Rb) (AV011; LA:GA=50:50; $M_n$=10,000-30,000 Da), and Poly(lactide-co-glycolide)-$NH_2$ (AI063) were obtained from Polyscitech®. Poly(ethylene glycol) methyl ether-block-poly(lactide-co-glycolide) (764760) was obtained from Sigma. The cationic lipid 1, 2-dioleoyl-3-trimethylammonium-propane (chloride salt) (DOTAP) was obtained from Avanti Polar Lipids (Alabaster, Ala., USA). Soybean lecithin consisting of 90-95% phosphatidylcholine was obtained from MP Biomedicals (Solon, Ohio, USA). All other chemicals were obtained from Sigma-Aldrich (St. Louis, Mo., USA) unless otherwise noted. Collagenase/Hyaluronidase and Bovine Pancreas DNase I-PBS solution were obtained from Stemcell Technologies. LIVE/DEAD® Fixable Yellow Dead Cell Stain Kit and ACK lysis buffer were obtained from Life Technology. Recombinant Murine IL-2 was obtained from PeproTech. αPD-1 (clone: RMP1-14) was from BioXcell. Potential antibodies which may be used for flow cytometric assays are listed in Table 1.

TABLE 1

List of antibodies used in flow cytometric analysis.

| Antibody | Clone | Fluorophore | Vendor |
|---|---|---|---|
| CD3 | 17A2 | APC-eFluor® 780 | eBioscience |
| CD4 | RM4-5 | Alexa Fluor® 488 | BD Biosciences |
| CD4 | GK1.5 | PE-Cyanine7 | eBioscience |
| CD8α | 53-6.7 | APC | BD Biosciences |
| CD8α | 53-6.7 | APC-eFlour780 | eBioscience |
| CD11c | N418 | PE-Cyanine7 | eBioscience |
| CD25 | PC61.5 | PE | eBioscience |
| CD45 | Clone: 30-F11 | eFluor® 450 | eBioscience |
| CD45R (B220) | RA3-6B2 | eFluor® 450 | eBioscience |
| F4/80 | BM8 | PE-eFluor® 610 | eBioscience |
| FOXP3 | FJK-16s | PE-eFluor® 610 | eBioscience |
| IFN-γ | XMG1.2 | Alexa Fluor® 488 | eBioscience |
| CD16/CD32 (Fc Block) | 2.4G2 | | BD Biosciences |

Mice

Six- to 8-week-old female C57BL/6 mice (The Jackson Laboratory) were used. All animal work was approved and monitored by the University of North Carolina (UNC) Animal Care and Use Committee. Sample sizes were calculated based on our preliminary data. We calculated an effect size of 1.821. The nonparametric analog of this effect size can be stated in terms of $p_1$=Pr (X<Y), or an observation in Group X is less than an observation in Group Y when $H_1$ is true. The null hypothesis being tested is $p_1$=0.5. For effect size 1.821, $p_1$=0.0$^{99}$. A sample size of at least 8 in each group will have 80% power to detect a probability of 0.099 that an observation in Group X is less than an observation in Group Y, using a Wilcoxon (Mann-Whitney) rank-sum test, with a 0.05 two-sided significance level. Mice were assigned to treatment groups based on cage numbers. The groups were not blinded. The efficacy data is representative one from three independent experiments. All animal work was approved and monitored by the University of North Carolina Animal Care and Use Committee.

Cell Culture 1

A B16-F10 cell line was acquired from the Tissue Culture Facility at the Lineberger Comprehensive Cancer Center at UNC. B16-F10 cells were cultured in Dulbecco's Modified Eagle's Medium (DMEM) (Gibco, Invitrogen, Carlsbad, Calif., USA) supplemented with 10% fetal bovine serum (FBS, Mediatech, Manassas, Va., USA) and penicillin/streptomycin (Mediatech).

Cell Culture 2

The B16-F10 cell line was acquired from ATCC, where the cell line was authenticated using morphology, karyotyping, and PCR based approaches and tested for mycoplasma. B16-F10 cells were cultured in Dulbecco's Modified Eagle's Medium (DMEM) (Gibco) supplemented with 10% fetal bovine serum (Mediatech), 100 U ml$^{-1}$ penicillin and 100 µg ml$^{-1}$ streptomycin (Mediatech), and 2 mML-glutamine (Gibco). The cell cultures were maintained below 50% confluence and early-passage cultures (between 4 and 9) were utilized for experiments.

Example 2: Formulation of Antigen-capturing Nanoparticles

Procedure 1

B16-F10 cells (1 million for each mouse) were seeded in T175 flask which contains 25 mL DMEM supplemented with 10% FBS and after being incubated overnight, the cells were washed with PBS for three times to get rid of FBS. Finally cells were cultured in plain DMEM medium and irradiated with 100 Gy using a Precision X-RAD 320 (Precision X-ray, Inc.) machine operating at 320 kvp and 12.5 mA. Subsequently, the B16-F10 cells were incubated for 48 to 72 hours in the incubator. After that, the supernatant was collected; spin down at 200 g for 5 min to get rid of debris.

Procedure 2

B16-F10 cells were seeded in T175 flask containing 25 mL of culture media and incubated overnight at 37° C. Cells were then washed three times with PBS and irradiated with 100 Gy photon radiation delivered using a Precision X-RAD 320 (Precision X-ray, Inc.) machine operating at 320 kvp and 12.5 mA. Subsequently, the B16-F10 cells were incubated in media without FBS for 48 hours. Following incubation, the supernatant was collected and spun down at 200 g for 5 min to remove insoluble cellular debris.

Example 3: Preparation of Antigen-Capturing Nanoparticles

Procedure 1

The nanoparticles were synthesized using a previously reported nanoprecipitation technique. Briefly, to prepare the pure PLGA NPs, 4 mg PLGA was dissolved in 1 mL acetonitrile (ACN) and then added dropwise into 3 mL of water and stirred at room temperature under vacuum. After the ACN has been evaporated, 20 mg resulting PLGA NPs suspension was added to the supernatant of irradiated B16-F10 cells immediately. And the mixture was allowed to stir gently for at least 2 h at room temperature. After then, the white floccus which means the antigens absorbed onto the nanoparticles was gently centrifuged at speed of 100 to 200 g. Last, the antigen-capturing PLGA NPs were resuspended with PBS, and collected. The antigen-capturing nanoparticles were used immediately.

To prepare the PLGA-lecithin-DOTAP core-shell nanoparticles from PLGA, soybean lecithin, and DOTAP, 4 mg PLGA was dissolved in 1 mL acetonitrile and then added dropwise into 3 mL of 4% ethanol aqueous solution which contains lecithin/DOTAP (7:3 molar ratio) with a weight ratio of 15% to the PLGA polymer and is pre-heated to 55.0° C. This solution is followed by 3 min of vortexing. 16 or 20 mg the resulting nanoparticles suspension were added to the supernatant of irradiated B16-F10 cells immediately. And the mixture was allowed to stir gently for at least 2 h under vacuum to remove ACN. After then, the white floccus which means the antigens absorbed onto the nanoparticles was gently centrifuged at speed of 100 to 200 g. Last, the antigen-capturing PLGA NPs were resuspended with PBS, and collected. The antigen-capturing nanoparticles were used immediately.

To prepare the antigen-capturing nanoparticles of PLGA-PEG-X NPs (X=mPEG, COOH, $NH_2$ or Maleimide), 20 mg PLGA was dissolved in 1 mL acetonitrile (ACN) and then added dropwise into 3 mL of water under stirring at room temperature under vacuum. After the ACN has been evaporated, 20 mg resulting PLGA-mPEG NPs suspension was added to the supernatant of irradiated B16-F10 cells immediately. And the mixture was allowed to stir gently for at least 2 h at room temperature. Then, nanoparticles were further purified by ultra-filtration (15 min, 500-800 g, Amicon Ultra, Ultracel membrane with 100,000 NMWL, Millipore, Billerica, Mass.) and Nanosep® Centrifugal Devices (300K cutting MW, OD300C34). The antigen capturing nanoparticles of PLGA-mPEG-Maleimide NPs, PLGA-mPEG-COOH NPs, PLGA-mPEG-$NH_2$ NPs was prepared similar as PLGA-mPEG NPs. 20 mg resulting PLGA NPs suspension was added to the supernatant of irradiated B16-F10 cells immediately right after dropping PLGA into water. And the mixture was allowed to stir gently for at least 2 h at room temperature to remove ACN. Then, nanoparticles were further purified by ultrafiltration (15 min, 500-800 g, Amicon Ultra, Ultracel membrane with 100,000 NMWL, Millipore, Billerica, Mass.). Then, the PLGA NPs were resuspended with PBS, and collected. The antigen-capturing nanoparticles were used immediately.

Procedure 2

The nanoparticles were synthesized using a previously reported nanoprecipitation technique (Govender, T., Stolnik, S., Garnett, M. C., Illum, L. & Davis, S. S., *J. Control Release* 57:171-85(1999)). Briefly, to prepare the PLGA NPs, PLGA (4 mg/mL) in acetonitrile (ACN) was added dropwise into 3 mL of endotoxin free water and stirred at room temperature under a vacuum until the ACN completely evaporated (approximately 3 hours). To prepare the X AC-NPs (X=mPEG, $NH_2$ or Mal (Maleimide)), PLGA-PEG-X (20 mg/mL) in ACN was added dropwise into 3 mL of endotoxin free water and stirred at room temperature under vacuum until the ACN completely evaporated.

Figure 14:
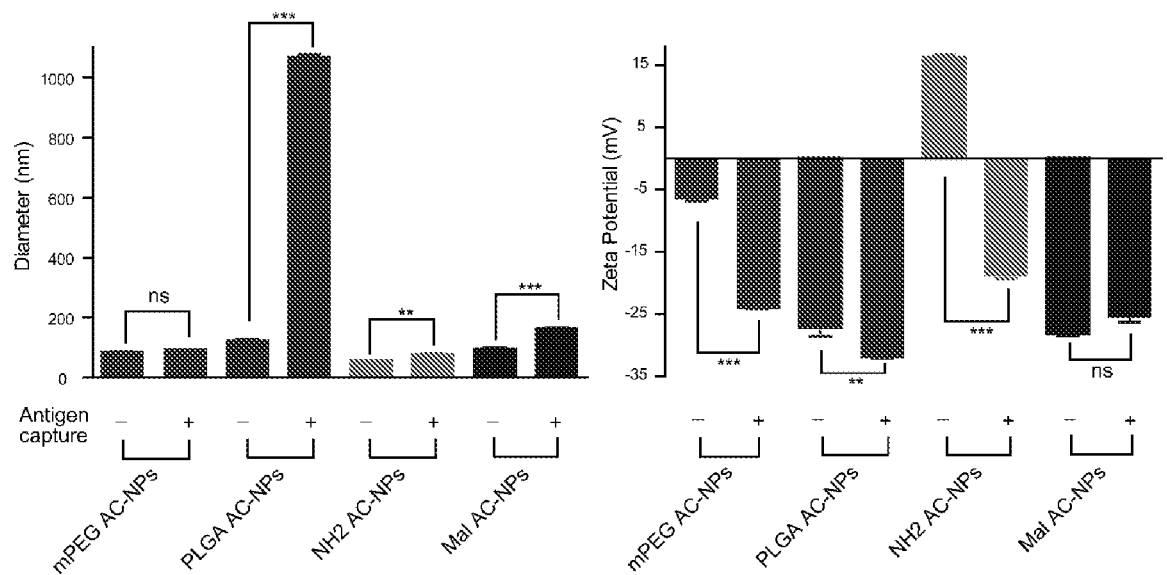
FIG. 14 shows AC-NPs' size and zeta potential following antigen capture. The difference of size and zeta potential of AC-NPs were compared by one-way analysis of variance (ANOVA) with Tukey's post-test. Data represent mean±standard error of the mean (SEM). P value: *, P<0.05; , P<0.01; *, P<0.005.

The resulting nanoparticle suspensions were immediately added to the supernatant of irradiated B16-F10 cells and the mixture was allowed to stir for 5-6 hours at room temperature. AC-NPs were purified by ultra-filtration at 500 g through an Ultracel membrane (100,000 NMWL Millipore) and a Centrifugal Device (300,000 NMWL, Nanosep). Collected AC-NPs were washed and re-suspended in endotoxin-free PBS. Vials and stir bars for nanoparticles preparation were autoclaved and washed with acetone and ACN before use. All nanoparticles were made under endotoxin-free condition. Intensity-average diameter ($D_h$, also known as hydrodynamic diameter) of AC-NPs and mean zeta potential (mean ζ) of AC-NPs were analyzed by dynamic light scattering and an aqueous electrophoresis method using a Zetasizer Nano ZS Instrument (Malvern, Inc.). Prior to the measurements, AC-NPs were diluted to 0.5 mg/mL with DI $H_2O$. All measurements were based on the average of three separate measurements. (FIG. 14).

Example 4: Mass Spectrum of Protein Identification of Complex Mixtures with Antigen-Capturing Nanoparticles (1D Separation)

Procedure 1

For mass spectrum, the nanoparticles were decomposed with 0.5 mL ACN and 0.1 mL DI $H_2O$. Then evaporate the ACN under vacuum. After that the solution was centrifuged at 200 g for 5 min to spin down the un-dissolved stuff. Take the supernatant for mass spectrum. Samples were digested using the FASP (Filter assisted sample preparation) protocol. This includes reduction, alkylation, and digested with trypsin. The peptides were extracted, lyophilized, and resuspended in 2% acetonitrile/98% (0.1% formic acid). The peptides were loaded onto a 2 cm long×360 μm o.d.×100 μm i.d. microcapillary fused silica precolumn packed with Magic 5 μm C18AQ resin (Michrom Biosciences, Inc.). After sample loading, the precolumn was washed with 95% Solvent A (0.1% formic acid in water)/5% Solvent B (0.1% formic acid in Acetonitrile) for 20 min at a flow rate of 2 uL/min. The pre-column was then connected to a 360 μm o.d.×75 μm i.d. analytical column packed with 22 cm of 5 μm C18 resin. The peptides were eluted at a flow rate of 250 nL/min by increasing the percentage of solvent B to 40% with a Nano-Acquity HPLC solvent delivery system (Waters Corp.). The LC system was directly connected through an electrospray ionization source interfaced to an LTQ Orbitrap Velos ion trap mass spectrometer (Thermo Fisher Scientific). The mass spectrometer was controlled by Xcalibur software and operated in the data-dependent mode in which the initial MS scan recorded the mass to charge (m/z) ratios of ions over the range 400-2000. The 10 most abundant ions were automatically selected for subsequent collision-activated dissociation. Each sample was analyzed by LC-MS/MS and the 2 runs are denoted R1 and R2.

All files were searched using MASCOT (Matrix Science, Ver. 2.3.02) via Proteome Discoverer (Thermo., Ver. 1.3.0.339) against a recently downloaded human FASTA database. The search parameters included peptide mass tolerance of 10 ppm, fragment ion tolerance of 0.6 mass units. The search allowed variable modifications for methionine oxidation and carbamidomethylation of Cys.

Procedure 2

For mass spectrometry, the AC-NP solutions were diluted 5-fold with ACN and mixed thoroughly to break down AC-NP formulations. ACN was then evaporated under vacuum. The solution was centrifuged at 200 g for 5 min and the supernatant was analyzed with mass spectrometry for protein identification. Samples were then digested using the Filter-assisted sample preparation (FASP) protocol which includes reduction, alkylation, and digestion with trypsin (Wisniewski, J. R., Zougman, A., Nagaraj, N. & Mann, M., Nat. Methods 6:359-62(2009)). The peptides were extracted, lyophilized, and resuspended in 2% ACN/98% aqueous formic acid (0.1% v/v). The peptides were loaded onto a 2 cm long×360 μm o.d.×100 μm i.d. microcapillary fused silica pre-column packed with Magic 5 m C18AQ resin (Michrom Biosciences). After sample loading, the pre-column was washed with 95% Solvent A (0.1% aqueous formic acid)/5% Solvent B (0.1% formic acid in ACN) for 20 min at a flow rate of 2 uL/min. The pre-column was then connected to a 360 μm o.d.×75 μm i.d. analytical column packed with 22 cm of 5 μm C18 resin. The peptides were eluted at a flow rate of 250 nL/min by increasing the percentage of solvent B to 40% with a Nano-Acquity HPLC solvent delivery system (Waters Corp.). The LC system was directly connected through an electrospray ionization source interfaced to an LTQ Orbitrap Velos ion trap mass spectrometer (Thermo Fisher Scientific). The mass spectrometer was controlled by Xcalibur software and operated in the data-dependent mode in which the initial MS scan recorded the mass to charge (m/z) ratios of ions over the range 400-2000. The 10 most abundant ions were automatically selected for subsequent collision-activated dissociation. Each sample was analyzed by LC-MS/MS and the 2 runs were denoted R1 and R2.

All files were searched using MASCOT (Matrix Science, Ver. 2.3.02) via Proteome Discoverer (Thermo., Ver. 1.3.0.339) against a recently downloaded mouse FASTA database. The search parameters included peptide mass tolerance of 10 ppm and a fragment ion tolerance of 0.6 mass units. The search allowed variable modifications for methionine oxidation and carbamidomethylation of Cys.

The numbers of captured proteins on different types of AC-NPs were compared and the overall P value was calculated by one-way analysis of variance (ANOVA) with Tukey post-test using the GraphPad Prism 5.0. P value: *, $P<0.05$; , $P<0.01$; *, $P<0.005$.

Example 5: Tumor Inoculation, Vaccination and Anti-PD-1/Anti-CTLA-4 Treatment

Figure 9:
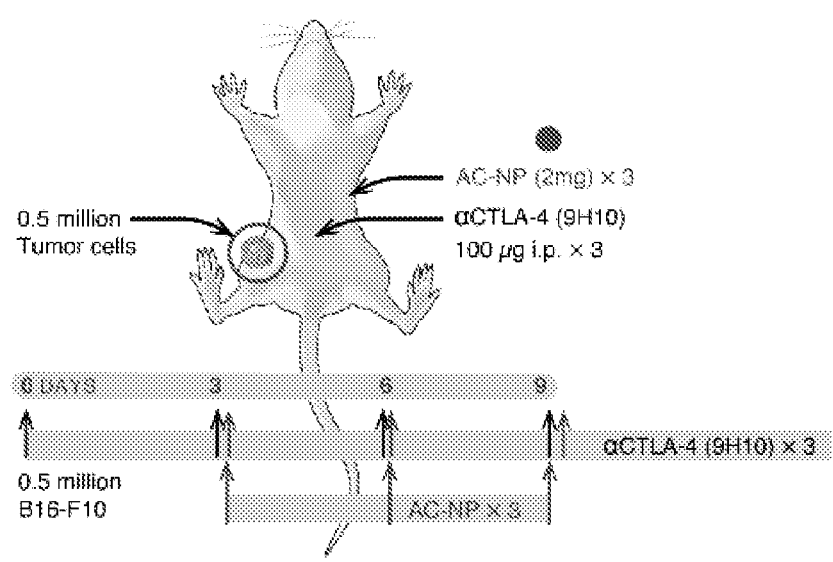
FIG. 9 shows the tumor model and treatment schedule of 2nd and 3rd vaccine.
Figures 13A, 13B, 13C:
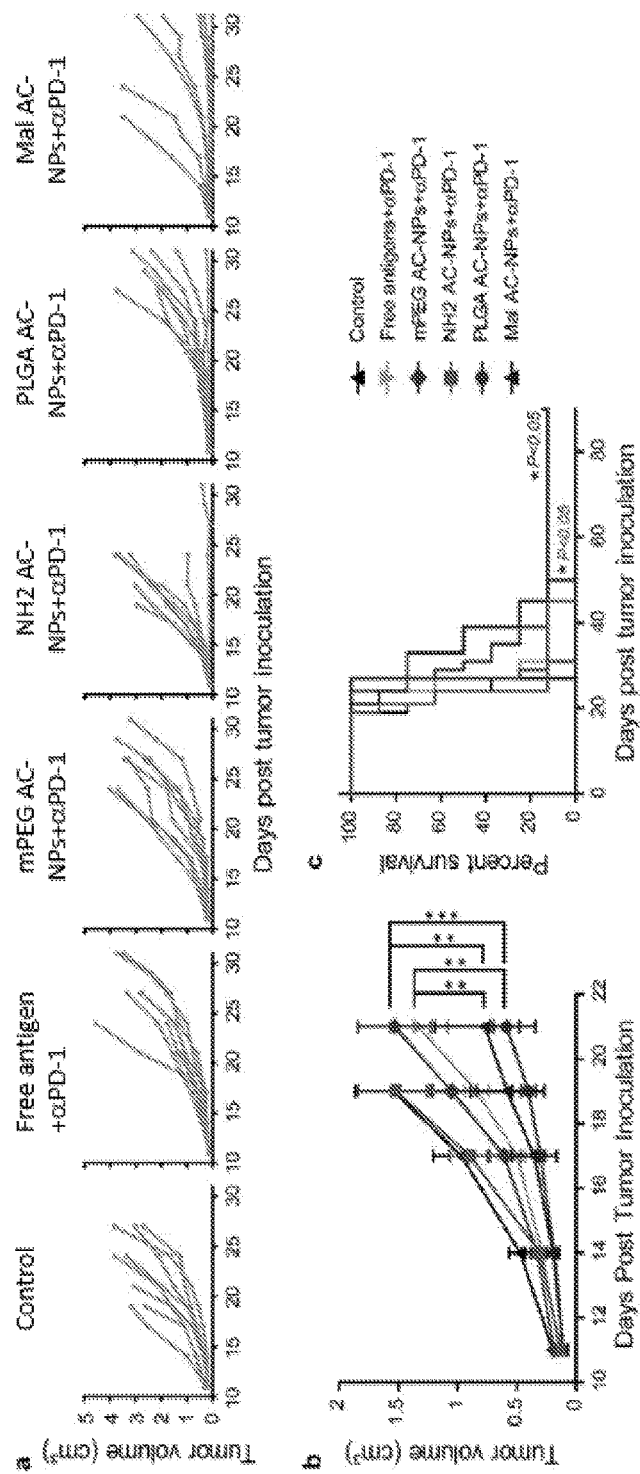
FIGS. 13(a)-13(c) show antigen coated AC-NPs act as tumor vaccines and enhance cancer immunotherapeutic response, similar to that of in vivo administration of AC-NPs.

Tumors were established in the left flank of C57BL/6 mice by injecting 50,000 B16-F10 cells in a 1:1 DMEM/Matrigel solution on day 0. On days 3, 6, and 9 after tumor inoculation, appropriate mice underwent subcutaneous injection of the antigen-capturing nanoparticles as described above in a volume of 200 μL. Control mice were subcutaneously injected with 200 μL of supernatant as described above. On the days 3, 6, and 9 after tumor inoculation, 100 μg of anti-CTLA-4 (9H10 clone, BioXCell, West Lebanon, N.H.) or anti-PD-1 (RMP1-14 clone, BioXCell, West Lebanon, N.H.) were delivered by intraperitoneal injection in 100 μL for each mouse. (FIGS. 9 and 15) Tumor volume was measured every other day until the tumor reached 2 cm diameter, at which point the animal was euthanized. The results of the experiments are shown in FIGS. 13(a)-13(c).

Example 6: Abscopal Experiment

Figure 3:
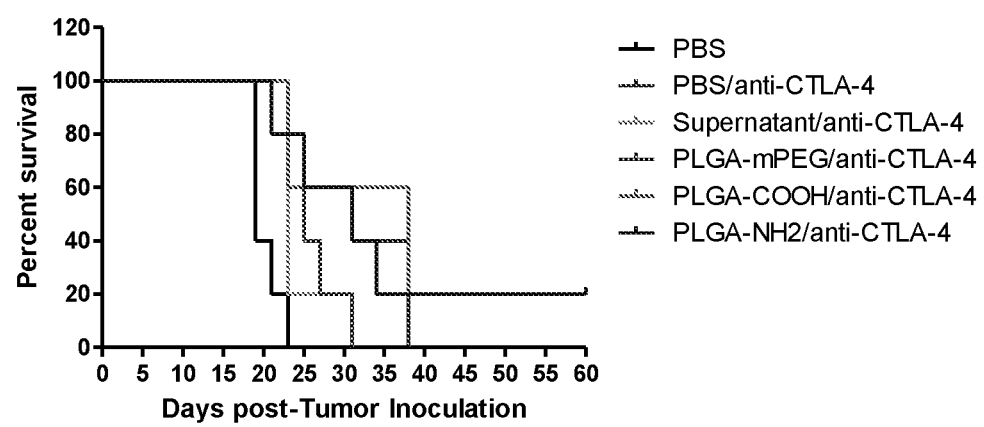
FIG. 3 shows a survival curve of antigen-capturing nanoparticles in combination with anti-CTLA-4 on C57BL/6 mice bearing B16F10 tumor xenografts (n=5).
Figure 4:
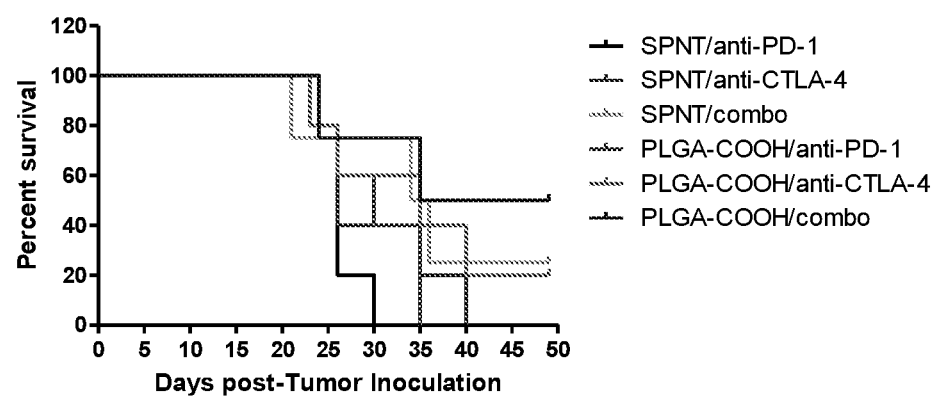
FIG. 4 shows a survival curve of antigen-capturing nanoparticles as cancer vaccine in combination with anti-CTLA-4, anti-PD-1 or combo on C57BL/6 mice bearing B16F10 tumor xenografts. (n=4-5).
Figure 5:
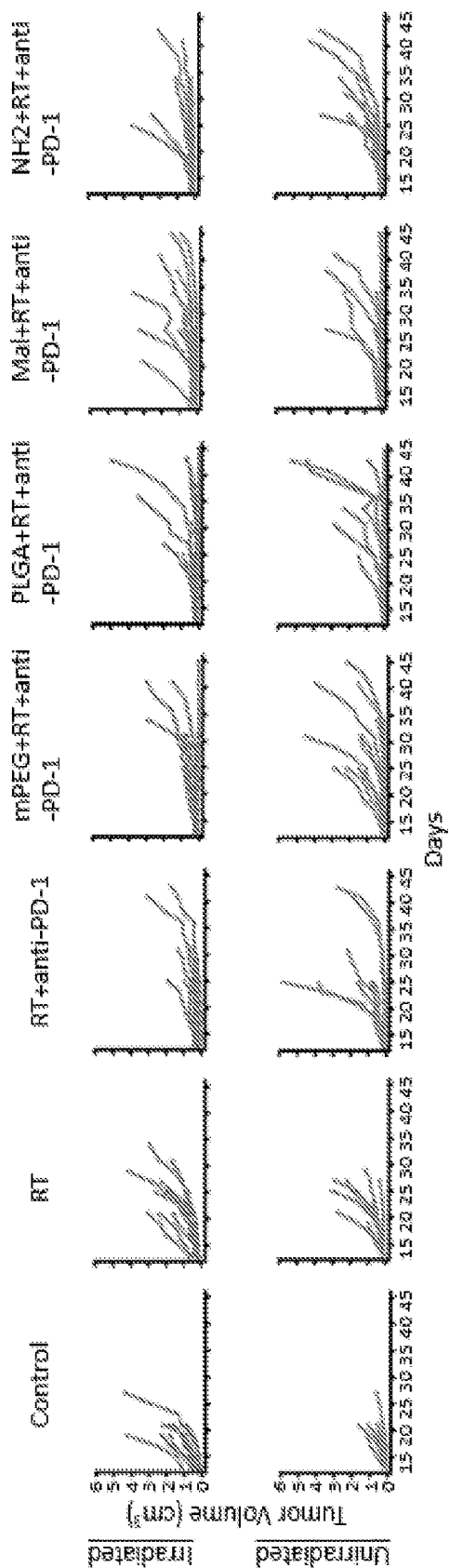
FIG. 5 shows tumor delay curves of abscopal effect. The individual B16-F10 tumor growth after radiation (RT) to the irradiated tumor (n=10), anti-PD-1+RT, mPEG+RT+anti-PD-1 (n=10), PLGA+RT+anti-PD-1 (n=10), Mal+RT+anti-PD-1 (n=9), and NH2+RT+anti-PD-1 (n=10) to the unirradiated tumor (n=9), or no (control) treatment (n=10).
Figure 6:
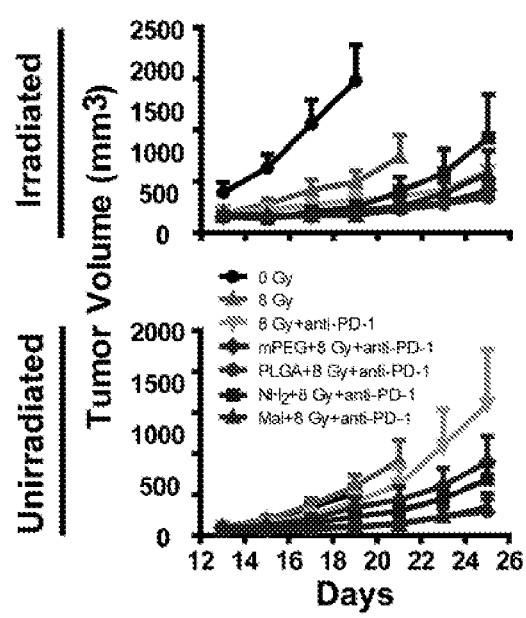
FIG. 6 shows tumor delay curves of abscopal effect. The B16-F10 tumor growth based on average tumor volume after radiation.
Figure 7:
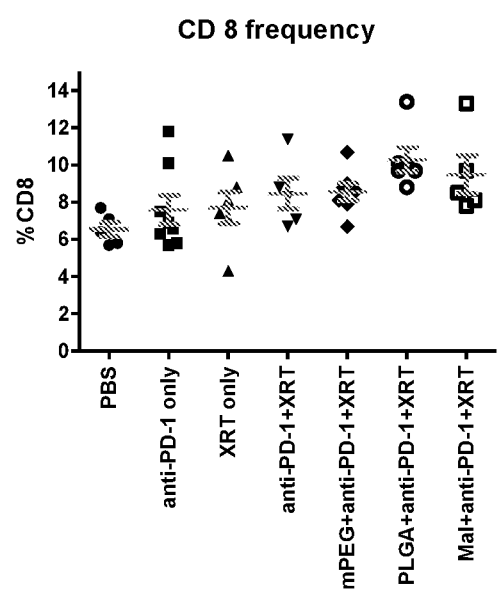
FIG. 7 shows CD8 T cell activation.
Figure 8:
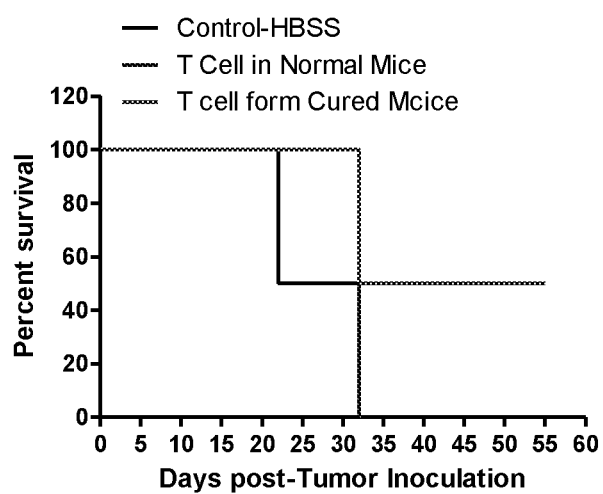
FIG. 8 shows adoptive T cell transfer.

C57BL/6 mice were injected s.c. with 50,000 B16-F10 cells which mixed with an equal volume of Matrigel (BD Biosciences), respectively, in the left flank on day 0 (primary tumor) and in the right flank on day 3 (secondary tumor). The right flank tumor site was irradiated with 8 Gy on three consecutive days starting on day 8. Blocking antibodies were given on day 5, 8 and 11. Antibodies used for in vivo immune checkpoint blockade experiments were given intraperitoneally at a dose of 200 μg per mouse and include: CTLA4 (9H10), PD-1 (RMP1-14) (BioXCell). Perpendicular tumor diameters were measured with a vernier caliper, and tumor volumes were calculated as length×width2×0.5. For irradiating, all mice were lightly anesthetized by i.p. injection of ketamine (100 mg/kg) and xylazine (10 mg/kg); mice were positioned on dedicated restraints, and the whole body was protected by lead shielding except for the area of the tumor to be irradiated. Radiotherapy was delivered to a field, including the tumor; a source-to-skin distance of 70 cm was set. Mice received three fractions of 8 Gy in consecutive days (FIG. 3). Anti-CTLA-4 or PBS was given i.p. at a dose of 200 μg/mouse (10 mg/kg) on days 12, 15, and 18. The nanoparticles (2 mg/mouse; PLGA-COOH NPs were suspended in 0.1% PVA and other nanoparticles was suspended in PBS.) were also intratumorally injected on the same three days.

Example 7: Adoptive T Cell Transfer Experiment

Procedure 1

The cells were extracted from the spleen of two cured mice from the experiment with total cell number of about 240 million. Then the extracted cells were injected i.v. into 4 mice with aliquot part. 6 days later, mice were inoculated with 50,000 B16-F10 cells and their survival curve was recorded.

Procedure 2

There are 2 cured mice in the $2^{nd}$ vaccine experiment. The cells were extracted from the spleen of these 2 mice with total cell number of about 240 million. (Note: The cells extracted from the spleen of 2 normal mice were about 200 million which was same as said in the protocol). Then the extracted cells were injected i.v. into 4 mice with aliquot part. (Note: With using antibody CD8a-APC (BDB553035) and the help of FACS facility in MEJB, there are 600K CD 8+ T cells in the sample (3 mL). In total it was a 20 mL cell suspension, so after calculation the total amount of CD 8+ T cells should be 4 million. Then 2 mice were killed and their spleens taken. Each spleen had 2 million CD 8+ T cells).

Example 8: Flow Cytometry: The CD 8+ T Cell Frequency

For flow cytometric analysis of in vivo experiments, blood, spleen, and tumor were harvested at either day 16 or 18 post tumor implantation. Single cell suspension were prepared and red blood cells were lysed using ACK Lysis Buffer (Life Technologies). Live/dead cell discrimination was performed using Live/Dead Fixable Aqua Dead Cell Stain Kit (Life Technologies). Cell surface staining was done for 20-30 min. Intracellular staining was done using a fixation/permeabilization kit (eBioscience.) T effector cells were phenotyped as CD8+CD44+, myeloid derived suppressor cells (MDSC) asCD11b+Gr−1+, and regulatory T cells (Treg cells) as CD4+FOXP3+. All flow cytometric analysis was done using an LSR II (BD) and analyzed using FlowJo software (TreeStar).

All Runs generated a large number of peptide and protein identifications (Table 2). In the Supernatant of non-irradiated and irradiated B16-F10 cells, about 550 proteins and 3700 PSMs were identified per run. Supernatant of irradiated B16-F10 cells+PLGA NPs/DOTAP NPs, about 320 and 235 proteins were identified per run. There appears to be real differences between the samples.

TABLE 2

Protein Identification of Complex Mixtures (1D Separation)

| Display Name | Run | Uniq Peptides | PSM | Proteins |
|---|---|---|---|---|
| Supernatant of non-irradiated B16-F10 cells | 1 | 2112 | 3734 | 533 |
|  | 2 | 2150 | 3735 | 528 |
| Supernatant of irradiated B16-F10 cells | 1 | 2045 | 3644 | 550 |
|  | 2 | 2076 | 3624 | 547 |
| Supernatant of irradiated B16-F10 cells + PLGA NPs | 1 | 1332 | 2882 | 325 |
|  | 2 | 1251 | 2574 | 308 |
| Supernatant of irradiated B16-F10 cells + DOTAP NPs | 1 | 1052 | 2755 | 238 |
|  | 2 | 1048 | 2585 | 231 |
| Supernatant of irradiated B16-F10 cells + Maleimide NPs | 1 | 684 | 881 | 197 |
|  | 2 | 517 | 647 | 166 |
| Supernatant of irradiated B16-F10 cells + NH$_2$ NPs | 1 | 172 | 180 | 93 |
|  | 2 | 160 | 164 | 75 |

Example 9: Efficacy of AC-NPs in Improving the Abscopal Effect

For tumor inoculation, 50,000 B16-F10 cells were suspended in DMEM, mixed with an equal volume of Matrigel (BD Biosciences), and subcutaneously injected on the left flank of C57BL/6 mice on day 0 (primary tumors) and the right flank on day 3 (secondary tumors). The left flank tumors (primary tumors) were irradiated with 8 Gy on days 8, 9, and 10 using an X-RAD 320. A lead shield protected the rest of the animal. αPD-1 blocking antibody (10 mg/kg) was intraperitoneally injected into animals on days 5, 8, and 11. AC-NPs (2 mg in 100 μL PBS) were injected into primary tumors on days 10, 11, and 12. Note PLGA AC-NPs were suspended in DI H$_2$O containing 0.05% polyvinyl alcohol (PVA). The detailed schedule can be found in FIG. 15(a).

Example 10: Antigen-Coated AC-NPs as Cancer Vaccines

For tumor inoculation, 50,000 B16-F10 cells in DMEM were mixed with an equal volume of Matrigel (BD Biosciences) and subcutaneously injected on the left flank of C57BL/6 mice on day 0. AC-NPs (2 mg) were loaded with tumor-derived antigen as described above and subcutaneously injected into the right flank of mice on days 3, 6, and 9. Free antigen injections were prepared by concentrating the supernatant from 1 million irradiated B16-F10 cells (the same amount and composition of supernatant used for AC-NP loading). The supernatant was concentrated using ultra-filtration through an Ultracel membrane (10,000 NMWL Millipore). αPD-1 blocking antibody (10 mg/kg) was intraperitoneally injected into animals on days 3, 6 and 9. The detailed schedule can be found in FIG. 15(b).

Example 11: Tumor Volume Measurements

Two perpendicular diameters were measured with a caliper and tumor volumes were calculated using the formula V=0.52×a×b$^2$, where a and b are the larger and smaller diameters, respectively. The tumor volumes were assessed every 2-3 days. Two independent researchers assessed tumor volume over time with one researcher blinded to the treatment group assignments. Statistical differences in average tumor growth curves were determined by two-way ANOVA using variables of time and volume. Differences in survival in each group were determined using the Kaplan-Meier method and the overall P value was calculated by the log-rank test using the GraphPad Prism 5.0. P value: *, P<0.05; , P<0.01; *, P<0.005.

Example 12: Distribution of Nanoparticles in Irradiated Tumor and Lymph Nodes

For tumor inoculation, 50,000 B16-F10 cells in DMEM were mixed with an equal volume of Matrigel (BD Biosciences) and subcutaneously injected on the left flank of C57BL/6 mice on day 0. The tumor was irradiated with 8 Gy using a Precision X-RAD 320 (Precision X-ray, Inc.) on days 8, 9 and 10. The rest of the body was protected with lead shielding. After the last dose of radiation on day 10, rhodamine B-labeled AC-NPs (2 mg) were injected into the irradiated tumor. The rhodamine B-labeled AC-NPs were prepared as described above with the exception that 5% wt/wt of PLGA-Rb was used for nanoprecipitation. The concentration of all labeled AC-NPs was quantified with a fluorescence spectrum photometer. The irradiated tumor and the draining inguinal lymph node were dissected 16 hours post treatment for flow cytometric analysis. Rhodamine B-labeled AC-NPs within lymph nodes were imaged with an IVIS imaging system. Uptake of AC-NPs into antigen presenting cells was assessed by flow cytometric analysis of single cell suspensions. These were stained with anti-mouse CD11c, F4/80, and B220 (Table 1). P value was calculated by analysis of unpaired t test using the GraphPad Prism 5.0. P value: *, P<0.05; , P<0.01; *, P<0.005.

Example 13: Flow Cytometric Analysis of Relative Abundance of Tumor Infiltrating T-Cell Populations Tumors were harvested on day 16 post tumor inoculation for flow cytometric analysis of in vivo experiments. Single cell suspensions were prepared using collagenase/hyaluronidase and DNase and red blood cells were lysed using ACK Lysis Buffer (Life Technologies). Live/dead fixable yellow dead cell staining kit (Life Technologies) was applied for live/dead cell discrimination. Before surface staining, samples were incubated with Fc Block for 5 min on ice, followed by surface staining with anti-mouse CD45, CD3, CD8, CD4 (Table 1). Cells were then fixed, permeabilized, and stained for intracellular FOXP3 (eBioscience). T effector cells were phenotyped as CD8$^+$ and regulatory T cells (T$_{reg}$ cells) as CD4$^+$FOXP3$^+$. All flow cytometric analysis was done using a Beckman Coulter CyAn ADP and analyzed using software Summit 5.2. Flow cytometric data analysis was performed in a blinded fashion. Two independent researchers performed collection and analysis of flow cytometric data. Differences were compared and the overall P value was calculated by analysis of unpaired t test using the GraphPad Prism 5.0. (P value: *, P<0.05; , P<0.01; *, P<0.005.) The representative plots of relative abundance of tumor infiltrating T cells were showed in FIG. 17.

Example 14: Flow Cytometric Analysis of IFN-γ Producing T Cells

Splenocytes were harvested on day 16-post tumor inoculation and plated for culture. The splenocytes were restimulated with tumor antigen as previously prepared for 72 hours. The supernatant was collected for cytokine analysis with ELISA. Splenocytes were washed and stained. Live/dead fixable yellow dead cell stain kit (Life Technologies) was applied for live/dead cell discrimination. For surface staining, samples were first incubated with Fc block for 5 min on ice and stained with anti-mouse CD3, CD8, CD4 (Table 1). Cells were then fixed, permeabilized, and stained for intracellular IFN-γ. All flow cytometric analysis was done using a Beckman Coulter CyAn ADP and analyzed using software Summit 5.2. The data were presented as the percentage of CD8$^+$IFN-γ$^+$ in CD8$^+$ cells, and the percentage of CD4$^+$IFN-γ$^+$ cells in CD4$^+$ cells. Differences were compared and the overall P value was calculated by analysis of unpaired t test using the GraphPad Prism 5.0. (P value: *, P<0.05; , P<0.01; *, P<0.005). The representative plots of relative abundance IFN-γ production T cells were shown in FIG. 18.

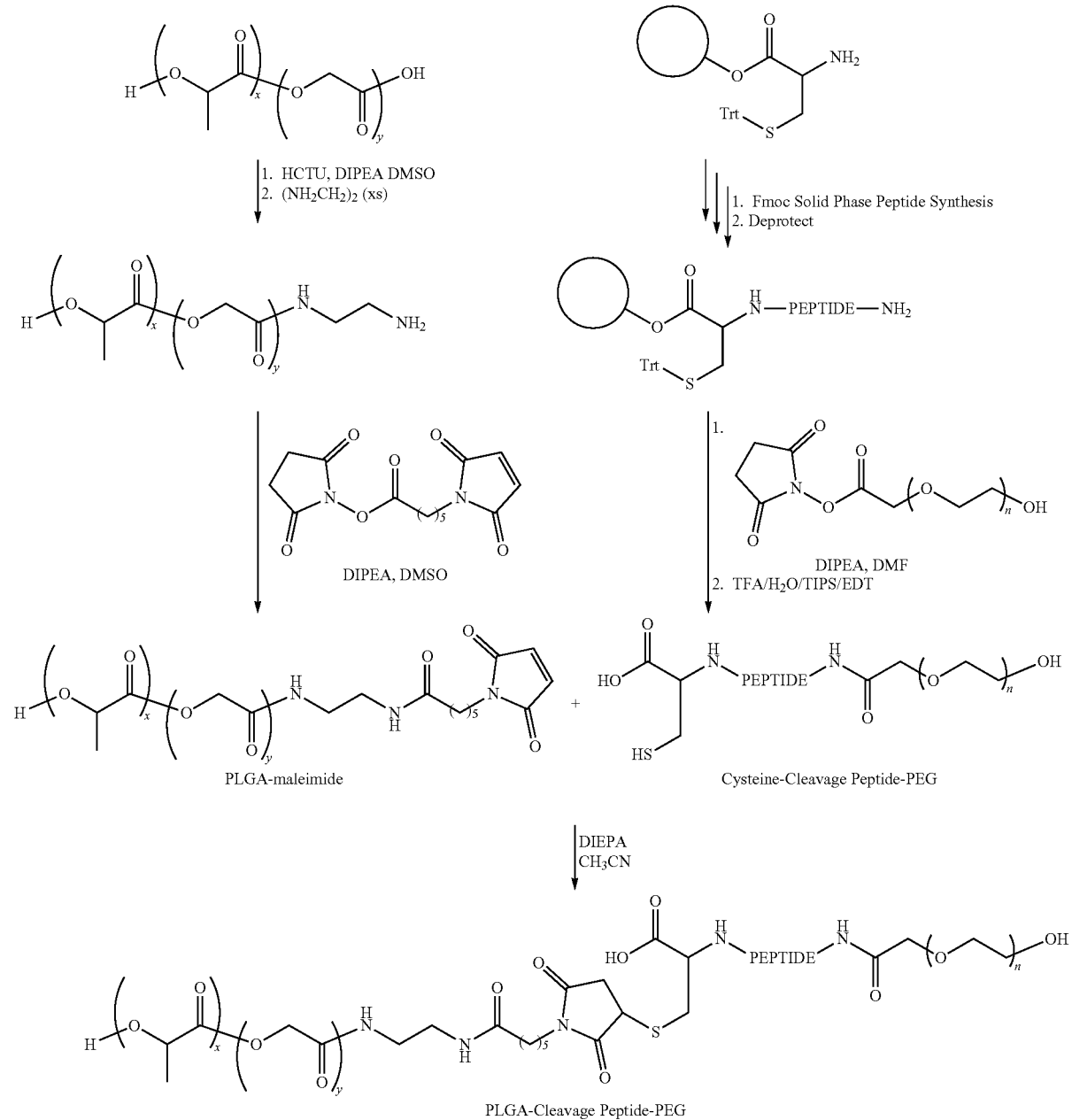

SCHEME 1

Scheme 1 depicts a convergent synthetic route for the preparation of a PLGA cleavage peptide-PEG as described herein.

Example 15: Synthesis of Antigen Capturing Polymer and Cleavage Peptide-PEG PLGA-Maleimide PLGA (25-34 kDa, 1:1 GA:LA, 500 mg, 14.7 µmol) was activated with HCTU (8.4 mg, 22.1 µmol) and DIPEA (1.9 mg, 147 µmol) in DMSO (2.5 mL). The solution was mixed for five minutes then ethylene diamine (2.6 mg, 44.1 µmol) was added. The reaction was mixed for 2 h then precipitated into chilled methanol. The precipitate was washed with additional methanol (3×30 mL) and then dried under vacuum overnight. Successful polymer functionalization was confirmed using quantitative ninhydrin test (recovered 480 mg, yield >96% functionalization).

The amine functionalized PLGA (480 mg, ~14.1 umols), 6-maleimide hexanoate succinimidyl ester (8.6 mg, 22.1 umols), and DIPEA (18.2 mg, 141 umols) were dissolved in DMSO (2.5 mL) and mixed overnight. The reaction was precipitated into MeOH and washed three times (30 mL MeOH). The polymer was dried and then tested for free amines using ninhydrin (negative result). Degree of maleimidation was determined using indirect Ellman's test that used the maleimides consumption of a constant concentration of 3-mercaptoethanol as an indicator for successful PLGA-maleimide functionalization (>98% functionalized, recovered 375 mg). Maleimide functionalized product was further confirmed by $^1$H NMR with a small doublet peak at ~6.8 ppm.

General Procedure for Cysteine-Cleavage Peptide-PEG

Using cysteine functionalized Wang resin (40 µmol cysteine, 72 mg resin), peptide sequences were made using standard Fmoc-solid phase peptide synthesis. After sequence synthesis, the resin was subjected to a final deprotection step (20% v/v Piperidine/DMF) and then washed with $CH_2Cl_2$. The resin was swelled again in DMF (1 mL), mixed with $PEG_{2000}$-NHS ester (114 mg, 52 µmols) and DIPEA (25.8 mg, 200 µmols), and allowed to react overnight. The resin was washed several times with $CH_2Cl_2$. The peptide-PEG was cleaved from the resin using cleavage cocktail (94% Trifluoro acetic acid, 2.5% $H_2O$, 2.5% ethane dithiol, and 1% tri-isopropyl silane), precipitated in ether, and purified by HPLC. Products were confirmed by LC-MS. Sequences and their predicted/detected masses are shown below. Since it is a polymer, the masses appear as a distribution. The most abundant peak from the mass distribution is shown. The Cysteine containing peptides can form non-thiol Michael reactive disulfides during storage. These disulfides are easily reduced back to reactive thiols using TCEP gel prior to reaction with PLGA-maleimide.

Caspase 3: $PEG_{2000}$-Asp-Glu-Val-Asp-Gly-Cys: predicted 662.5 (z=+4), found 662.7.

Matrix metalloproteinase 2 (MMP2): $PEG_{2000}$-Gly-Pro-Leu-Gly-Ile-Ala-Gly-Gln-Cys: predicted 824.9 (z=+4), found: 825.1; predicted 1193.1 (z=+2), found 1193.2; predicted 663.2 (z=+4), found 663.3.

Cathepsin B: $PEG_{2000}$-Gly-Phe-Leu-Gly-Cysteine: predicted 850.33 (z=+3), found 851.0; predicted 649.2 (z=+4), found (649.4).

General Procedure for PLGA-Cleavage Peptide-PEG

A slight excess of PLGA-maleimide (76 mg, ~2.2 µmols) and DIPEA (1.4 mL, 10.5 µmols) was dissolved in 500 µL $CH_3CN$. Cysteine-Cleavage Peptide-PEG (~5 mg, 2.0 µmols) was added to this solution and allowed to react in a thiol-Michael click reaction for 4 h. A small aliquot of the reaction was tested for residual free cysteines that did not react using an Ellman's test. No residual thiols were detected. The reaction was dried using nitrogen stream and then washed with methanol (2 mL).

Example 16: Formulation Stability of PLGA-PEG & PLGA-Maleimide

The optimal ratio of PLGA-PEG and PLGA-Maleimide that provides both particle stability and blocks particle phagocytosis was determined. PLGA-PEG and PLGA-Maleimide polymers were mixed at different wt % ratios in $CH_3CN$ and then formed into nanoparticles via nanoprecipitation. Particles were washed and then dispersed at 5 mg/mL in PBS (1×). Polydispersity (PDI) was recorded over five days using dynamic light scattering to determine particle stability. Large increases in PDI are indicative of poor stability. Particles composed of at least 40% PLGA-PEG and 60% PLGA-maleimide showed good stability. Lower amounts of PEGylation results in instability (20:80 aggregation).

Example 17: Determination of Phagocytosis Block

Figure 22A:
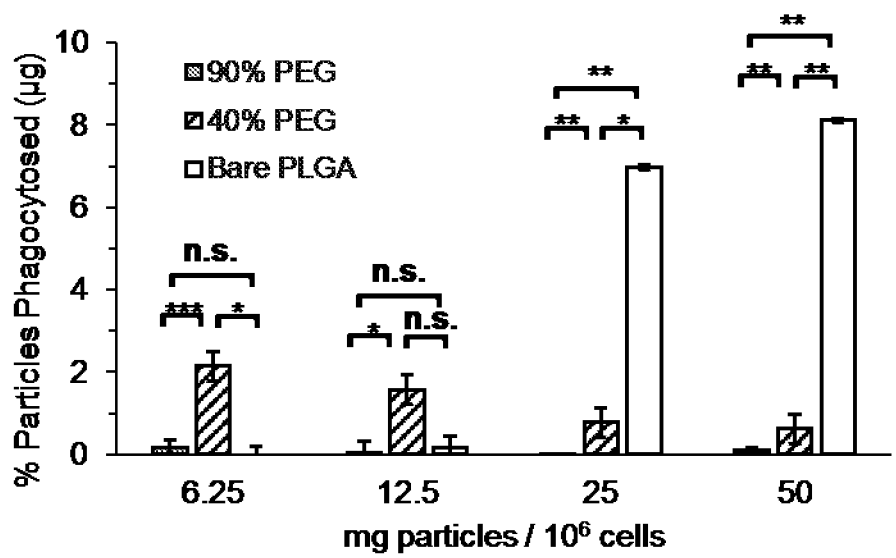
FIGS. 22(a) and 22(b) shows data used in determining particle uptake.
Figure 22B:
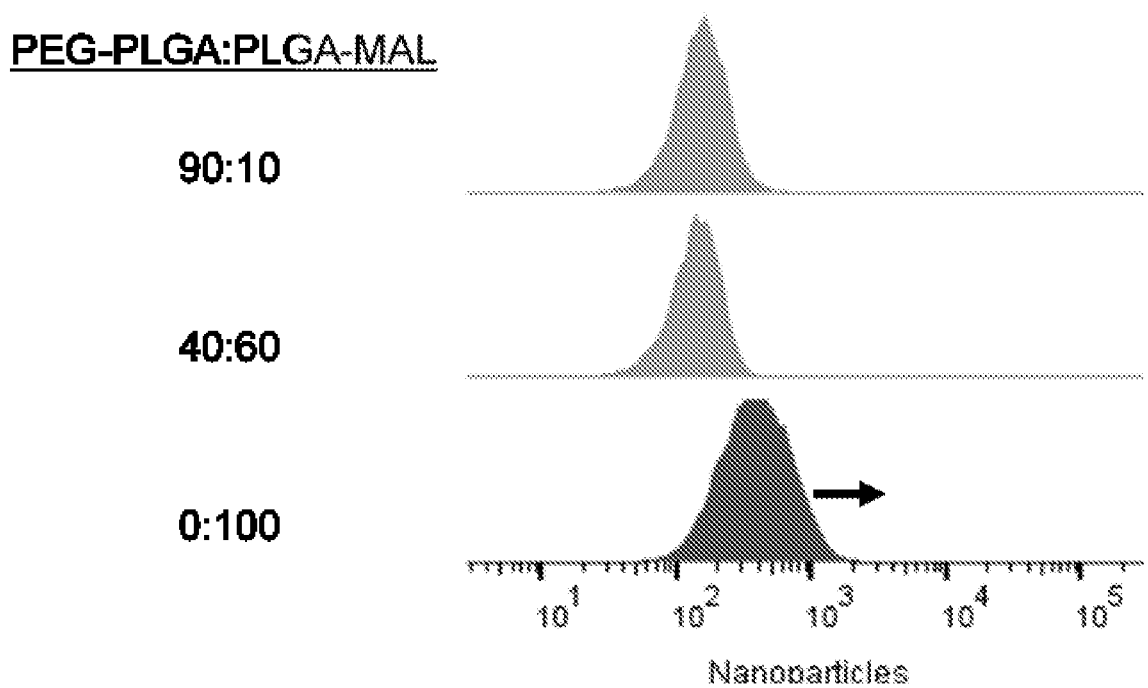

Nanoparticles were formed with different ratios of PLGA-PEG and PLGA (at least 10% PLGA Rhodamine and the remainder PLGA-Maleimide, e.g., 40:60 particle is 40 wt % PEG-PLGA, 50 wt % PLGA-Maleimide, and 10 wt % PLGA-Rhodamine). Raw264.7 macrophages were exposed to the particle formulations at various doses for four hours. The cells were then washed and nanoparticle uptake determined using cell associated fluorescence (top-plate reader fluorescence counts using a standard curve or bottom-flow cytometry) using the encapsulated PLGA-rhodamine. At higher particle doses, macrophages phagocytosed significantly more non-PEGylated particles than either the 40% PEGylated or 90% PEGylated particles (FIG. 22(a)). Macrophages exposed to a low dose of particles (5 mg/$10^6$ cells) showed increased bare particle uptake (bottom row) compared to the PEGylated particles (FIG. 22(b)). These results indicate the stable 40% PEGylated particle can also efficiently block uptake relative to the bare particle.

Example 18: MMP2 Cleavage of Cysteine-Cleavage Peptide-PEG

Figure 23:
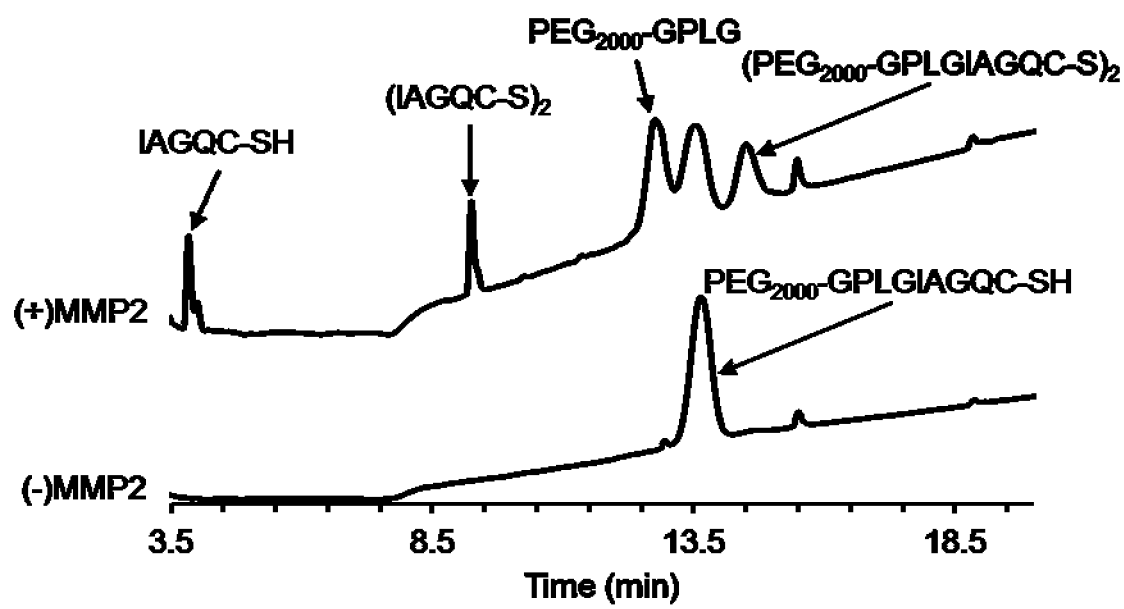
FIG. 23 shows the MMP2 cleavage of Cysteine-Cleavage Peptide-PEG.

The PEG-peptides were examined as substrates for their target proteases (FIG. 23). The MMP2 sensitive peptide-PEG (1 mg/mL) was reduced (to break up disulfides formed during storage) using TCEP gel and then treated with human MMP2 (10 ng/µL) in HEPES buffered saline for 4 h. The bottom row shows no cleavage, while the top row shows peptide fragmentation ($PEG_{2000}$-GPLG//IAGQC-SH). Some disulfide products [$(IAGQC-S)_2$ and ($PEG_{2000}$-GPL-GIAGQC-S)$_2$] were formed but these will not be expected after thiol ether bioconjugation to the PLGA-maleimide.

Example 19: Protocol for Generation of Viron Replicon Particles (VRP) Infected Dendritic Cell (DC) Vaccines Venezuela Equine Encephalitis Virus matures and activates DCs and increases homing to lymph nodes. Optionally, the radiation damaged tissue/cells and nanoparticles may be substituted for virus.

Reagents and Materials

6-Well Ultra Low Attachment Plates (Coming No. 3471, Fisher cat #07-200-601), DC media, recombinant mouse GM-CSF (10 ug/ml; Peprotech cat #315-03), recombinant mouse IL-4 (10 µg/mL; Peprotech cat #214-14), sterile polypropylene transfer pipettes, PBS, RPMI-1H (RPMI-1640, 1% FBS, 10 mM HEPES, filtered), and Thaw Mix, which is made in bulk and keep in stock.

Methods

Day −1

1. Prehydrate 6-well low cluster plates with 2 mL media per well for 10-15 min at 37° C. Use one well per $2\times10^6$ cells.
2. Retrieve the cryopreserved DCs from the liquid nitrogen tank. Quickly thaw the cells in a 37° C. water bath for 1-2 min. Spray down the tubes with 70% EtOH, wipe with a KimWipe and transfer to tissue culture hood.
3. Use a sterile polypropylene transfer pipette to gently remove the cells and transfer to a 50 mL conical tube containing an equal amount of DC media. Use up to 5 mL of cells for each 50 mL conical tube.
4. Wash out the cryovials with cold media and pool with the cells.
5. Add 8 mL of media per mL of frozen cells to the 50 mL conical tube of cells. For example: For 4 thawed tubes of cells (4 mL), add the cells to 4 mL of Thaw Mix and bring the total volume up to 40 mL with cold media.
6. Spin the cells at 1200 rpm for 10 min at 4° C.
7. Carefully aspirate the wash with a pipette, without decanting, and gently resuspend the cells in 10-20 mL of media. Spin for 5 min at 1200 rpm at 4° C.
8. Aspirate the wash and resuspend to $10^6$ cells/ml in media (100% recovery assumed).
9. Supplement the media with 5 ng/mL GM-CSF and 5 ng/mL IL-4. Gently mix the cells.
10. Remove the hydration media from the 6-well low cluster plates. Plate the DCs at $2\times10^6$ cells (2 mL) per well. Incubate overnight (18-24 h) at 37° C. Further maturation of the DCs with LPS and/or TNFα may be necessary, but the nanoparticle approach may be used to establish a baseline. In humans, use IFNα and IL-6 in addition to TNFα.

Notes: Recovery of cryopreserved DCs is typically 50-90%. Optionally, thaw twice the number of DCs that is needed for the experiment. Important considerations when working with cryopreserved cells include keeping everything cold, being gentle when pipetting the cells, and when using the freeze mix, keeping the cells cold and washing them thoroughly. Keep pipetting to a minimum until the cells are plated. Do not touch the bottom of the wells with the pipet as this scratches the surface and will allow the DCs to adhere.

Day 0

1. Use a polypropylene transfer pipette to harvest the DCs and transfer to a 50 mL conical tube. Wash each well with 2 mL of cold PBS or RPMI-1H. Save the plates for the infections. Optionally, harvest three wells at one time, add HBSS back to those wells, and then move on to the next three wells. After all the wells are harvested, optionally go back and remove the wash and pool it with the cells.
2. Spin the cells for 10 min at 1200 rpm at 4° C.
3. Resuspend the cells in an appropriate amount of cold RPMI-1H for counting.
4. Count the DCs.
5. Dilute DCs to $1\times10^6$/ml in RPMI-1H.
6. Use RPMI-1H to rehydrate the 6-well low cluster plates that were used for culturing the DCs overnight. Incubate at 37° C. for 5-10 min.
7. Remove hydration media and add 1 mL ($10^6$ DCs per well).
8. Determine the inoculum of the nanoparticles. Prepare the VRP inoculum by adding $10^7$ infectious units per well in a 100-200 ul volume. Use PBS to dilute the VRP. The multiplicity of infection (MOI) will be 10.
9. Infect for 2 hours at 37° C. Gently agitate the plates every 20-30 min to mix the DCs with the VRPs.
10. After infection, add 5 mL cold RPMI-1H to each well of the 6-well plates. Transfer to 50 mL conical tubes (optionally, pool similarly infected DCs) and spin for 8-10 min at 1200 rpm, 4° C. During the spin, add 5 mL cold RPMI-1H wash to each well (optionally, verify that no cells are sticking to the plate by looking under a microscope).
21. After the spin, carefully aspirate the wash using a 10 mL pipette (or decant) and resuspend cells by flicking the tube. Add the 5 mL media wash from the 6-well plates and spin cells again for 8-10 min at 1200 rpm, 4° C.
22. Resuspend cells with PBS and spin 5 min at 1200 rpm, 4° C.
23. Resuspend cells at $1\times10^7$ cells/mL in PBS with 1-2% of protein (preferred proteins are heat inactivated bovine serum albumin or normal mouse serum) for the subcutaneous injections. Keep on ice until ready to inject. Pre-wet the syringe with a sterile 1-2% protein PBS to prevent the DCs from adhering to the syringe. Avoid reducing the protein surrounding the DCs once "pulsed" with peptide/lysate/nanoparticle/other proteins. For human injections use 150-200 micrograms/mL peptide for pulsing and wash it off just before injection. Keep it cold and in the presence of 2% human serum albumin.

Vaccination of Mice with DCs

Materials

Ketamine solution (13 uL ketamine+19 uL xylanine+18 uL saline=50 uL per mouse), 0.3 mL insulin syringes, 1 mL syringes with needle, electric clippers, 70% EtOH bottle, eye lubricant and Q-tips.

1. Place DC vaccine on ice.
2. Inject the mice with 50 uL of ketamine solution i.p and transfer to a clean cage. Optionally, work with one cage of mice at a time. The mice should go under in 2-3 minutes.
3. Use a Q-tip to apply eye lubricant to the anesthetized mice to help protect their eyes while under anesthesia.
4. Shave the right side of the chest over the mammary glands. Wipe down the shaved area with 70% EtOH.
5. Use 0.3 mL insulin syringes to inject 100 uL of DCs ($10^6$) subcutaneously in the mammary fatpad. Control mice will receive 100 uL of saline only.
6. Repeat the above steps for the remaining mice.
7. Check mice daily for one week.

Example 20: Generation of Murine Bone Marrow-Derived Dendritic Cells

This protocol generates proliferative myeloid cells that can be cryopreserved in a less than mature state. One does not have to freeze these cells down; they may be further matured.

Materials and Reagents

100×20 mm round tissue culture dishes, 5 ml syringes, 25 gauge needles, 50 mL conical tubes, dissecting tools (scissors, scalpel, large and small forceps), dissecting plate with pins, 6-Well Ultra Low Attachment Plates (Corning No. 3471, Fisher cat #07-200-601), recombinant mouse GM-CSF (10 µg/mL; Peprotech cat #315-03), recombinant mouse IL-4 (10 µg/mL; Peprotech cat #214-14), disposable transfer pipettes, freeze mix (90% FBS, 10% DMSO, filter sterilize and store at 4° C.), cryovial tubes, cryogenic freezing chamber (Mr. Frosty®), HBSS/10 mM HEPES DC Media: 500 mLs final: 10% FBS and RPMI 1640 with:
- 2 mM L-glutamine, 10 mM HEPES, 0.1 mM NEAA, 1 mM Sodium Pyruvate (100× stocks)—5 mLs each
- 1% Pen-Strep (100× stock)—5 mLs
- 50 mM 2-ME (1000× stock)—500 μL ACK lysis buffer:
- 8.29 g $NH_4Cl$ (0.15M)
- 1 g $KHCO_3$ (1.0 mM)
- 0.0372 g $Na_2EDTA$ (0.1 mM)
- Add 800 mL $H_2O$ and adjust pH to 7.2-7.4 with 1N HCl
- Add $H_2O$ to 1 liter
- Filter, sterilize, and store at room temp or 4° C.

Bone Marrow Harvest
1. Spray down the hood and all materials with EtOH.
2. Pour an adequate amount of RPMI-10% media (50 mL) into a 50 mL conical tube for a working solution. For washing out the marrow cavities, use 2 mL media/femur and 1 mL media/tibia.
3. Pipette 10 mL of RPMI 10% media into one of the round tissue culture dishes. This will be the dish for holding the dissected bones.
4. Obtain a BL/6 mouse and put it in the $CO_2$ chamber. Turn on the $CO_2$ for 1 minute. Turn off the $CO_2$ and allow the mouse to sit for another minute. Perform a cervical dislocation to confirm death.
5. Transfer the mouse to the tissue culture hood. Pin the mouse down to the dissecting plate. Wash the mouse with EtOH.
6. Cut the skin away from the ankle. Separate the skin from the leg muscle by blunt dissection, and then remove the skin with the scissors.
7. Cut the distal patellar tendon with the scissors. Pull the quadriceps muscle up and away from the femur using the forceps. Blunt dissect the posterior muscles by inserting the scissors between the muscle and the femur and then opening the scissors.
8. Barely open the scissors and scrape the anterior tibia to remove any adherent fascia.
9. Cut the distal tibia just above the ankle. Do not cut through the entire leg. Using one set of forceps, pull the distal tibia up and away from the knee while stabilizing the knee joint with the other forceps. Remove the tibia completely and transfer it to the round tissue culture dish containing media.
10. Twist off the distal articular cartilage of the femur using the forceps.
11. Pull the femur up and away from the hip joint and rotate to disarticulate from the joint. Once the femur is disarticulated, use scissors to cut any attaching ligaments and fascia. Transfer the femur to the round tissue culture dish with media.
12. Fill a 5 mL syringe containing a 25 gauge needle with 3 ml of RPMI-10% FBS media. Using scissors, remove the proximal metaphysis of the femur. Insert the needle into the proximal end of the femur. Slowly inject 1 mL of media into the marrow cavity while moving the needle up and down, pooling the media into an empty round dish. Remove the needle and insert it into the distal end of the femur and inject another 1 mL of media over the round dish. Dispose of the femur into another empty round dish.
13. Using scissors, cut the distal tibia near the articulation with the fibula. Insert the needle into the distal end and inject the remaining 1 mL of media over the dish containing the pooled marrow. Discard the tibia into the round disposal dish.
14. Repeat steps 12 and 13 for the remaining bones.

DC Preparation
1. Filter the bone marrow cells through a 40 um cell strainer into a 50 mL tube (optionally, after harvesting the marrow from each mouse as leaving the bone marrow in the plate for a long time may cause the cells to adhere). Wash the dish with 5 mL of media and filter into the 50 mL tube. Spin the tube for 5 min at 1200 rpm, 4° C.
2. Remove the supernatant fluid and resuspend the cell pellet in 1.5 mL of ACK lysis buffer/mouse. Incubate at room temp for 2 min.
3. Add 10 mL of media/mouse to the ACK solution. Spin for 5 min at 1200 rpm.
4. Remove supernatant and resuspend cells in 10 mL of media. If cell clumps are evident, filter again through a 40 μm strainer into a 50 mL conical tube. Remove 10 uL for counting (usually 15-25×$10^6$ cells per mouse, but for larger mice there may be 30-40×$10^6$ cells per mouse). Spin cells again for 5 min at 1200 rpm, 4° C.
5. Hydrate the 6-well low cluster plates with 2 mL media per well. Incubate at 37° C. for at least 10 min to prevent the cells from adhering to the plate.
6. Resuspend the cell pellet at 1.0×$10^6$ cells/ml in DC media. Add 0.5 mL of GM-CSF to final concentration of 20 ng/mL. Total volume in each well is then 1.5 mL.
7. Remove hydration media from 6-well low cluster plates and add 1×$10^6$ cells (1.0 mL) to each well. Incubate at 37° C./5% $CO_2$.

Notes: For best results use only polypropylene transfer pipets to move cells. Additionally, incubation of the cells in a low-traffic incubator is important as constant fluctuations in temperature and $CO_2$ from opening and closing the incubator is detrimental to the culture and results in low DC yield.

Day 3:
1. Add 1.5 mL of RPMI-10 with 20 ng/mL GM-CSF and 20 ng/mL IL-4 to each well. Final volume per well is 3.0 mL with final concentration of 10 ng/mL GM-CSF and 10 ng/mL IL-4. Swirl plate gently to mix media with cells. Do not mix by pipetting as this can nonspecifically induce DC maturation (Gallucci et al., Nat. Med. 5:1249 (1999)).

Day 5:
1. Add 3.0 mL of RPMI-10 with 10 ng/mL GM-CSF and 10 ng/mL IL-4 to each well. Final volume per well is 6.0 mL with final concentration of 5 ng/mL GM-CSF and 5 ng/mL IL-4. Do not mix by pipetting.

Day 7:
1. Harvest the cells with the polypropylene transfer pipet and transfer to 50 mL or 250 mL conical tubes. Harvest 3 wells at one time, then add 5 mL of cold HBSS/10 mM HEPES back to the wells if there are many sticky cells.
2. Once all the cells have been harvested, remove the HBSS/10 mM HEPES wash and add to the DCs. Spin cells for 10 min at 1200 rpm, 4° C.
3. Resuspend DCs in 10 mL HBSS/10 mM HEPES and count. Spin DCs for 5 min at 1200 rpm, 4° C.
4. Resuspend DCs to 5-10×$10^6$ per mL in Freeze Mix and add 1 mL per cryovial tube. Freeze the cells in a Cryogenic Freezing Container at −80° C. Transfer DCs to liquid nitrogen within 2 days.

Resuspending Cytokines

All cytokines are purchased from Peprotech in 10 ug quantities minimum and come lyophilized. To resuspend, pulse spin the tube to collect all the cytokine at the bottom of the tube. Add 100 uL of sterile hospital water and finger vortex for 10 seconds. Let stand at room temperature for at least ten minutes. Then add 900 uL of RPMI-10 for a final volume of 1 mL at a concentration of 10 μg/mL. Aliquot the cytokines in 30-50 μL volumes into 0.6 mL sterile microfuge tubes. Store the cytokines at −20° C.

That which is claimed:

1. A method of enhancing or inducing an immune response in a subject having cancer comprising:
   administering to the subject a nanoparticle comprising:
   a core, wherein said core comprises Polymer-X-J, wherein,
   X is PEG' or a linker; and
   J is a reactive group, wherein at least a portion of said J is present on the surface of said core and at least one of said J present on said surface is covalently bound to PEP-PEG", and wherein PEP is a protein sequence, wherein said protein sequence is a protease sensitive protein sequence;
   wherein the nanoparticle is free from any antigen prior to the administration to the subject.

2. The method of claim 1, wherein said cancer is at least partially necrotizing.

3. The method of claim 1, further comprising administering an adjuvant.

4. The method of claim 3, wherein said adjuvant is selected from the group consisting of lipopolysaccharides, monophosphoryl lipid a, imiquimod, resiquimod, thiolated nucleic acids, and DMXAA.

5. The method of claim 1, wherein said cancer releases Cathepsin, Caspase, or MMP2.

6. The method of claim 1, wherein said nanoparticle is administered in an amount between 10 µg to 1 g.

7. The method of claim 1, wherein said subject has undergone previous treatment for said cancer.

8. The method of claim 7, wherein said cancer is brain cancer, non-small cell lung cancer, small cell lung cancer, esophageal cancer, gastric cancer, pancreatic cancer, colorectal cancer, renal cell carcinoma, bladder cancer, prostate cancer, breast cancer, non-hodgkins lymphoma, hodgkin's lymphoma, anal cancer, head and neck cancer, or melanoma.

9. The method of claim 8, wherein said cancer is non-small cell lung cancer, breast cancer, or melanoma.

10. The method of claim 2, wherein said nanoparticle binds at least one antigen released from said at least partially necrotizing cancer.

11. The method of claim 10, wherein said subject has undergone previous treatment for said cancer, wherein said previous treatment is selected from the group consisting of radiation, chemotherapy, cryotherapy, hyperthermia, and surgery.

12. The method of claim 11, wherein said treatment is radiation.

13. The method of claim 10, wherein said antigens comprise immune checkpoint inhibitors or molecules that can further enhance antigen presentation and increase T cell activation.

14. A method of treating, alleviating, ameliorating, relieving, delaying onset of, inhibiting progression of, reducing severity of, or reducing incidence of one or more symptoms or features of a disease, disorder, or condition in a subject comprising administering to a subject a nanoparticle comprising:
   a core,
   wherein said core comprises Polymer-X-J,
   wherein, X is PEG' or a linker; and J is a reactive group,
   wherein at least a portion of said J is present on the surface of said core and at least one of said J present on said surface is covalently bound to PEP-PEG", wherein PEP is a protein sequence, wherein said protein sequence is a protease sensitive protein sequence, and
   wherein the nanoparticle is free from any antigen prior to the administration to the subject;
   wherein the administration of the nanoparticle enhances an immune response.

15. The method of claim 14, wherein the disease, disorder, or condition is a cancer.

16. The method of claim 15, wherein the cancer is brain cancer, non-small cell lung cancer, small cell lung cancer, esophageal cancer, gastric cancer, pancreatic cancer, colorectal cancer, renal cell carcinoma, bladder cancer, prostate cancer, breast cancer, non-hodgkins lymphoma, hodgkin's lymphoma, anal cancer, head and neck cancer, or melanoma.

17. The method of claim 16, wherein the cancer is brain cancer, non-small cell lung cancer, breast cancer, or melanoma.

18. A method of treating, alleviating, ameliorating, relieving, delaying onset of, inhibiting progression of, reducing severity of, or reducing incidence of one or more symptoms of a cancer in a subject comprising
   providing a nanoparticle comprising a core,
   wherein said core comprises Polymer-X-J, wherein, X is PEG' or a linker; and J is a reactive group,
   wherein at least a portion of said J is present on the surface of said core and at least one of said J present on said surface is covalently bound to PEP-PEG",
   wherein PEP is a protein sequence, wherein said protein sequence is a protease sensitive protein sequence, and
   wherein the nanoparticle is free from any antigen; and
   administering the nanoparticle to a subject,
   wherein said cancer is at least partially necrotizing, and the nanoparticle binds at least one antigen released from said at least partially necrotizing cancer.

19. The method of claim 18, wherein the cancer is brain cancer, non-small cell lung cancer, small cell lung cancer, esophageal cancer, gastric cancer, pancreatic cancer, colorectal cancer, renal cell carcinoma, bladder cancer, prostate cancer, breast cancer, non-hodgkins lymphoma, hodgkin's lymphoma, anal cancer, head and neck cancer, or melanoma.

* * * * *